United States Patent
MacMahon et al.

(10) Patent No.: US 6,878,128 B2
(45) Date of Patent: Apr. 12, 2005

(54) FLUID EXCHANGE SYSTEM FOR CONTROLLED AND LOCALIZED IRRIGATION AND ASPIRATION

(75) Inventors: John M. MacMahon, Mountain View, CA (US); Thomas G. Goff, Menlo Park, CA (US); Brian K. Courtney, Palo Alto, CA (US)

(73) Assignee: Kerberos Proximal Solutions, Mountain View, CA (US)

( * ) Notice: Subject to any disclaimer, the term of this patent is extended or adjusted under 35 U.S.C. 154(b) by 0 days.

(21) Appl. No.: 10/819,409

(22) Filed: Apr. 6, 2004

(65) Prior Publication Data

US 2004/0193099 A1 Sep. 30, 2004

Related U.S. Application Data

(62) Division of application No. 10/198,718, filed on Jul. 17, 2002, now Pat. No. 6,827,701.
(60) Provisional application No. 60/306,315, filed on Jul. 17, 2001.

(51) Int. Cl.[7] .......................... A61M 5/178; A61M 3/00; A61M 1/00; A61M 5/00
(52) U.S. Cl. .......................... 604/38; 604/43; 604/121; 604/246
(58) Field of Search .............................. 604/6.11, 6.12, 604/19, 30–38, 43, 118, 121, 181, 236, 246; 417/341–343, 539

(56) References Cited

U.S. PATENT DOCUMENTS

| | | | |
|---|---|---|---|
| 3,923,065 A | 12/1975 | Nozick et al. | |
| 4,457,747 A | * 7/1984 | Tu | 604/6.12 |
| 4,655,746 A | 4/1987 | Daniels et al. | |
| 4,714,460 A | 12/1987 | Calderon | |
| 4,794,928 A | 1/1989 | Kletschka | |
| 4,909,783 A | * 3/1990 | Morrison | 604/30 |
| 5,462,529 A | 10/1995 | Simpson et al. | |
| 5,653,690 A | 8/1997 | Booth et al. | |
| 5,827,229 A | 10/1998 | Auth et al. | |
| 5,833,650 A | 11/1998 | Imran | |
| 5,938,645 A | 8/1999 | Gordon | |
| 5,957,883 A | * 9/1999 | Lin | 604/36 |
| 5,989,263 A | 11/1999 | Shmulewitz | |
| 6,013,085 A | 1/2000 | Howard | |
| 6,022,336 A | 2/2000 | Zadno-Azizi et al. | |
| 6,146,370 A | 11/2000 | Barbut | |
| 6,206,868 B1 | 3/2001 | Parodi | |
| 6,231,588 B1 | 5/2001 | Zadno-Azizi | |
| 6,254,563 B1 | 7/2001 | Macoviak et al. | |
| 6,290,689 B1 | 9/2001 | Delaney et al. | |
| 6,488,671 B1 | 12/2002 | Constantz et al. | |
| 2001/0039411 A1 | 11/2001 | Johansson et al. | |

FOREIGN PATENT DOCUMENTS

| | | |
|---|---|---|
| WO | WO 99/45835 | 3/1999 |
| WO | WO 00/76390 | 6/2000 |

* cited by examiner

*Primary Examiner*—Michael J. Hayes
(74) *Attorney, Agent, or Firm*—Townsend and Townsend and Crew LLP

(57) ABSTRACT

The control of fluid introduction into and out of body conduits such as vessels, is of great concern in medicine. As the development of more particular treatments to vessels and organs continues it is apparent that controlled introduction and removal of fluids is necessary. Fluid delivery and removal from such sites, usually referred to as irrigation and aspiration, using fluid exchange devices that control also need to be considerate of potential volume and/or pressure in the vessel or organ are described together with catheter and lumen configurations to achieve the fluid exchange. The devices include several electrically or mechanically controlled embodiments and produce both controlled and localized flow with defined volume exchange ratios for fluid management. The applications in medicine include diagnostic, therapeutic, imaging, and uses for the introduction or removal of concentrations of emboli within body cavities.

9 Claims, 19 Drawing Sheets

LAMINATE FLOW (VELOCITY APPROACHES ZERO AT THE WALL)

LENGTH OF ARROWS INDICATES MAGNITUDE OF VELOCITY

GRIP LEVER RELAXED

GRIP LEVER ACTIVATED

TWO SIDES MECHANICALLY LINKED

TOP VIEW OF TRACK LAYOUT FOR TRIGGER TRAVEL

ATTACHED TO TRIGGER

FLUID EXCHANGE SYSTEM FOR CONTROLLED AND LOCALIZED IRRIGATION AND ASPIRATION

CROSS-REFERENCE TO OTHER APPLICATIONS

This application is a divisional of U.S. patent application Ser. No. 10/198,718, filed on Jul. 17, 2002 now U.S. Pat. No. 6,827,701, which is a continuation-in-part of U.S. Provisional Application Ser. No. 60/306,315, filed on Jul. 17, 2001. The priority of the prior applications are expressly claimed, and the disclosure of each of these prior applications are hereby incorporated by reference in their entirety.

FIELD OF THE INVENTION

The devices and related methods of the invention relate to the controlled introduction and removal of fluids in diagnostic, therapeutic and imaging applications within the body. Specifically, the invention relates to the advantageous use of a fluid exchange device in combination with a catheter to produce a system for controlled aspiration and irrigation and the selective and localized exchange of fluids within a body conduit, for example, in the diseased region of a blood vessel having a blockage or lesion. The devices of the invention, and the methods enabled by the use of the devices, have several different components that can be used individually or integrated into a system for use within an organ and within the vasculature of the body where controlled and localized irrigation and aspiration are performed together as a therapeutic procedure or in tandem with a separate therapeutic procedure.

BACKGROUND OF THE INVENTION

Irrigation and aspiration are clinically important in many surgical procedures when fluids are selectively introduced into and removed from a target site within the body, usually while a surgery or other therapeutic medical procedure is performed. When the site of the therapeutic treatment is inside a body cavity or in the vasculature of the body, such as in a blood vessel, the irrigation and aspiration functions require special apparatus and methods. Surgical and percutaneous systems that both irrigate and aspirate have been developed, and some of these systems are catheter-based such that the introduction and removal of fluids is performed within an organ or a vessel by using the catheter as the conduit to introduce and remove fluids from a target site. As will be readily appreciated, the catheter allows the control elements to be remotely located, e.g., outside the body while the actual irrigation and aspiration functions are selectively provided within the body by selectively orienting the distal end of the catheter to the target site. In such cases, as is the case in open surgeries, the irrigation and aspiration functions accompany a therapeutic procedure that is performed at the target site along with the irrigation and aspiration.

Catheter-based irrigation and aspiration systems are unique in many respects due to their use in clinical situations where blockages or lesions exist inside a blood vessel, such as a coronary or carotid artery, and dangers arise from the creation and release of emboli within the vessel. In many intravessel therapeutic procedures, the danger from the creation of emboli is an unavoidable aspect of the therapeutic procedure. For example, lesions of atherosclerotic plaques inside a blood vessel are treated by several therapeutic procedures including endarterectomy, atherectomy, the placement of intravessel stents, balloon angioplasty, surgical ablation of the lesion, thrombectomy, OCT, dialysis shunt clearing and others. However, while each of these procedures has great therapeutic value in treating the lesion, each carries the risk of creating emboli during the procedure. As with any procedure conducted in the cardiovascular system, the risk is particularly great where plaque dislodged from inside a blood vessel can travel to the brain causing serious brain injury or death. For example, treating lesions of the carotids necessarily involve high risk. Currently, carotid treatments are attempted together with deployment of a filter to attempt to track emboli generated by or released from a carotid lesion. Unfortunately, crossing a carotid lesion with a filter or other structure can generate a cerebral ischemia or stroke. Schlueter et al. 2001, Circulation 104 (17) II-368. Moreover, studies have shown that merely crossing a carotid lesion with a guide wire can generate emboli. Al-Mubarak et al.: Circulation 2001 October 23:104 (17): 1999–2002. Also, some lesions carry such a high risk of generating emboli that therapeutic treatments are attempted only in the most severe cases. Where a chronic total occlusion exists, the diagnosis is particularly poor because it is impossible to place a structure distal of the occlusion such that emboli generated by the removal of the occlusion can be captured before circulating in the bloodstream. Such occlusions can only be treated by removing the occlusion from the proximal side, where emboli removal is uniquely difficult. Accordingly, if the capability existed to dramatically reduce the dangers of emboli creation during therapeutic procedures inside a vessel or organ of the body, the existing procedures would be safer and more widely practiced, and new procedures would be performed.

A variety of systems to contain and remove emboli have been proposed wherein a portion of a vessel that contains a lesion is segregated by two occluding members, typically two balloons, which are inflated proximate and distal to the lesion to effectively seal the inside of a region of the vessel containing a lesion prior to treatment of the lesion. Once treatment is complete, embolic particles such as dislodged plaque are removed by applying suction between the balloons. However, the tissue affected by a lesion is notoriously delicate and the treatment of the lesion has the capability to generate or release emboli whenever any mechanical manipulation of the lesion occurs. The generation and/or release of emboli is a concern virtually anytime a structure is passed through a susceptible vessel. Such circumstances include the placement of a balloon or stent, the placement of a filter, or simply the use of a catheter or guide wire for imaging, diagnostic, or any other procedure. In many procedures, the internal portion of a vessel is occluded to provide a segregated region of a vessel through which fluid does not flow. Moreover, virtually anytime structures are inserted into the vessel, the generation of release of emboli is a concern. For example, in the common practice of placing a stent inside an artery, a filter may be placed distally of the stent to attempt to collect emboli generated when the stent is expanded to engage plaques or lesions inside the vessel. All devices placed distal involve the crossing of the lesion. All crossings of lesions create emboli of some quantity and significance. Such systems cannot protect the patient against the potential harm inherent in the placing the device. Additionally, once the stent is in place, the filter must be removed by pulling it through the portion of the vessel in which the stent has been inserted. This carries the risk that the filter will impact the vessel and cause the release of emboli and/or contact the stent and either displace the stent or similarly cause the release of embolic particles. The use of occluding members of any type has certain drawbacks. Anytime a structure is used as an occlusive member inside a vessel, the structure must deform the vessel from the inside to create a seal about the periphery thereof with the internal surface of the vessel. For example, to make the seal tight enough to prevent the passage of fluid and emboli past the balloon, the expansion of the balloon typically deforms the vessel outward and may disrupt plaque in and about the point of contact between the vessel and the balloon. Moreover, any plaque that becomes dislodged outside the barrier formed by the balloon is released into the blood stream because there is no mechanism distal of the balloon to remove the emboli. For this reason, irrigation and aspiration proximate to the lesion are particularly important.

To create a segregated region of a vessel, a two-balloon system may be used. However, certain disadvantages of a two-balloon system also arise from the placement of balloons on both sides of a lesion and the nature of the blood flow that occurs in the region of the vessel containing the lesion once the balloon is removed. At the point of contact between the balloon and the vessel, plaque may be compressed underneath the balloon and may become dislodged upon reestablishment of flow through the vessel. Furthermore, many clinicians have observed that the region distal of a lesion is more likely to exhibit plaque formation than the region proximal of a lesion. Thus, the use of an occluding member distal of a lesion does not eliminate the risk of creating emboli that may enter the vessel. The risk is particularly great when a second balloon is used because the balloon is not advantageously placed for the removal of emboli created by the use of the balloon itself and because the balloon must be removed by passing it across the lesion upon completion of a procedure. This drawback is present in all circumstances when a balloon is advanced across a lesion because, when any occluding member is placed distally of the lesion, the occluding member must be drawn back across the lesion to remove the occluding member at the end of a procedure. Each passage of an occluding member across the lesion, even in a retracted or deflated state, carries a substantial risk that additional emboli will be produced.

Also, the placement of two balloons requires additional time to inflate the second balloon and adds to the complexity of a device due to an additional lumen that must be incorporated into the catheter to inflate the balloon. In a finite number of cases, the occluding member that is distal of a lesion, and is required to retain emboli in a defined area within the vessel, has been observed to fail, thereby releasing the emboli into the bloodstream. Because the second balloon is relied upon to prevent the flow of emboli past the region of the vessel containing the lesion, the failure of the balloon is a critical event that threatens the health of a patient undergoing the procedure. Furthermore, due to geometric constraints, the second balloon often acts as the guide wire as well. When delivering tools to perform the therapeutic or diagnostic procedure within the vessel, the balloon may move and disrupt the vessel wall. Introduction of tools and other manipulations of a distally located balloon can also result in deflating the balloon or otherwise causing the balloon to lose patency on the interior of the vessel.

Anytime that a balloon is placed distal to a lesion, the contact between the balloon and the lesion carries the risk of damaging the vessel. For these reasons, the use of balloons inside the vessel is preferred to be minimized and the length of time and extent of contact between a balloon and the inside of a vessel should be reduced. Ideally, the balloon or other occluding member could be placed proximal to a lesion so that the area containing the lesion would be isolated. To achieve this, the irrigation and aspiration functions would have to be provided by a structure that is positioned distal of the occluding element, such that the occluding element could be placed proximal of the lesion, and the aspiration and irrigation functions achieved distal of the occluding member.

Even under existing technologies where aspiration and irrigation are applied in a catheter based system, the parameters of fluid flow, as well as the placement of the aspiration and irrigation ports relative to an occluding member, are important to the physiological outcome for any given procedure. For example, removal of fluid and/or embolic particles by simple suction from within a body conduit may only remove a portion of the fluid present in the vessel and may leave emboli in place even if all of the fluid is removed and replaced. Deposits of plaque and other debris that may exist inside a vessel have a tendency to adhere to one another and particulate emboli tend to adhere to the sidewalls of the vessel. Thus, a system that provides limited fluid exchange is particularly unlikely to achieve a complete removal of emboli. Also, given that the interior walls of a vessel may have been contacted from within during a therapeutic procedure, a high likelihood exists that additional particles may be dislodged upon the establishment of a robust fluid flow through the vessel.

Ideally, a system for aspirating and irrigating the interior or a vessel or organ would provide both fluid exchange and fluid flow parameters that are at least similar to that experienced during ordinary physiological functions and preferably would create a turbulent fluid flow that would proactively assist in the removal of particles and other emboli. Such a system would require both a catheter element that achieved aspiration and irrigation as well as a fluid exchange apparatus that would be coupled with the catheter to produce the desired fluid flow rates and other fluid parameters. Because of the wide variation in intravessel procedures and the location of disease, an irrigation and aspiration system would also be particularly useful if the catheter element could be selectively positioned along a specified length of a vessel where emboli may be created together with operation of the fluid exchange apparatus to control the irrigation and aspiration flow. This capability in the catheter element is most readily created with only a single balloon system having a separate, movable, irrigation and aspiration catheter.

In the prior art two-balloon system described above, where a region of a vessel is segregated by a pair of balloons located both proximally and distally of a lesion, the area of fluid flow is limited to the region defined by the placement of the two balloons. The problem is particularly acute when a vessel is treated with a procedure that installs a stent or manipulates the plaque in a vessel, such as with an angioplasty, where the lesion is physically manipulated as part of the therapeutic treatment. Assuming that the therapeutic treatment is successful, the vessel is treated by virtue of expanding the interior volume and promoting the flow of blood through the vessel. Under these circumstances, the portions of the vessel distal of the lesion have been contacted by a balloon and are then exposed to a higher volume of fluid flow than existed before the procedure. In the context of a typical patient, a vessel which had become slowly blocked due to the deposit of plaque over a large number of years has been expanded by the treatment of the lesion and this therapeutic treatment at an upstream point subjects the region in which the lesion is located and those downstream internal portions to a rate and volume of blood flow that has not been experienced in the many years since the vessel began to become occluded.

Under these circumstances, an additional risk exists that plaques located downstream from the lesion will be dislodged and will enter the circulation causing serious injury.

As with ordinary irrigation and aspiration in an open surgery, the irrigation and aspiration that are applied through existing catheter systems are typically regulated only by setting the positive or negative pressure that is applied to the aspiration or irrigation lumen of the catheter and is in turn communicated to the distal end of the catheter to insert or remove fluid respectively. However, to create the specific fluid flow parameters that maximize the removal of emboli and the fluid displacement within a vessel, thereby establishing fluid change in the vessel in the most physiologically relevant manner, a specialized fluid exchange device would have to be created to regulate the fluid flow parameters of both the irrigation and aspiration functions of the system.

An ideal irrigation and aspiration system could be an additive component to several other apparatus that are used in therapeutic, diagnostic, or imaging applications in the body such that the capability of the system would not be exclusive of other technologies that have been applied to enhance the safety of an intravessel procedure. Several different approaches apart from irrigation and aspiration have been attempted to physically capture emboli downstream at a lesion, most notably through the use of filters. However, filters have inherent drawbacks that cannot be completely eliminated. For example, embolic particles smaller than the filter pore size, commonly on the order of 100 microns evade filters, which must not be so small that physiologically important elements such as red and white blood cells are captured by the filter. Also, particles larger than the pore size tend to become trapped in the filter such that the filter itself becomes an occlusive element and blood flow through the filter is impeded. Also, as described above for occluding structures, whenever a filter is introduced distally to the lesion in a vessel, a finite probability exists that the removal of the filter will generate emboli. Still further, where a stent is placed at a lesion, the movement of the filter past the stent and through the vessel has the capability to catch or displace the stent.

Although certain portions of the discussion herein are directed towards a preferred embodiment of the apparatus of the invention used in an intravessel procedure, the devices and methodologies of the invention can readily be applied to non-vessel sites within the body such as within any body conduit such as an ear canal, colon, intestine, the trachea, lung passages, sinus cartilages, or any internal volume wherein a controlled and localized irrigation and aspiration function are desired. For example, in a diagnostic colonoscopy an endoscope may be introduced to aid in optical visualization of the site. However, the colon responds to fluid pressure changes and thus while trying to clear the field the tissue of note may move. To aid in this diagnostic situation, a controlled introduction of a clear fluid could be introduced in concert with an equivalent aspiration of dirty fluid. As such, the tissue may remain in the field of view while the process occurs. For imaging purposes the introduction of a contrast agent while simultaneously extracting an equivalent fluid will allow a vessel or organ to maintain its normal fluid level and pressure. As the imaging is completed, the same system could then return a more normal fluid to the site while extracting the foreign contrast agent. Imaging "pig-tail" catheters are presently used to introduce contrast agents to vascular system, even though radiopaque contrast agents are known to maintain a level of toxicity (Solomon, *Kidney International,* 1998, vol. 53, pp. 230–242). If the field of contrast was introduced and extracted as proposed by Courtney, et al., the patient's exposure would be substantially reduced.

SUMMARY OF THE INVENTION

The present invention provides control of both irrigation and aspiration functions at a selected location within a body cavity or conduit, such as a target region of a blood vessel. The region of the vessel to which an irrigation and aspiration function are provided may include both a therapeutic treatment site, the site proximal to the placement of a balloon, or a length of a vessel both proximal to and distal of a lesion wherein a surgical treatment was performed, where a diagnostic or therapeutic procedure caused the insertion of a dye or other solution, such as a clot dissolver, or where a total chronic occlusion occurs. Because the irrigation and aspiration functions are performed simultaneously, the fluid exchange apparatus of the invention is able to simultaneously regulate both irrigation and aspiration in a manner that advantageously controls the fluid flow rates and fluid flow parameters. This capability can be achieved both by controlling the flow rates using an electronic control system, as well as providing a mechanical apparatus that controls irrigation and aspiration flows when actuated by a user. When the catheter and fluid exchange device are combined into the system of the invention, the combination provides unique capabilities for treating or diagnosing a lesion contained within a vessel. For example, the lesion may be pre-treated prior to the therapeutic treatment which typically comprises ablation of a lesion or placement of a stent or expansion of the diameter of the vessel, i.e., through an angioplasty procedure. In a diagnostic embodiment, dye or other diagnostic markers can be infused distally of the occluding member and proximate to the lesion while avoiding the potential hazards of passing a collapsed balloon across the lesion. This provides a diagnostic capability which has substantially reduced risk relative to a therapeutic treatment that requires expansion of an occluding member distal of the lesion. Because of the added safety margin, the diagnostic procedures can be more readily performed without the risk of producing emboli and thus are a more available complement to the therapeutic procedure.

Preferably, the system of the invention includes a catheter element having specific features designed to facilitate the desirable fluid flow parameters when connected to the fluid exchange apparatus. Ideally, when coupled with an apparatus that inherently provides controlled and regulated fluid flows for both aspiration and irrigation, the catheter works in tandem with the apparatus to create both controlled and localized irrigation and aspiration through a catheter-based system. For example, the apparatus of the invention allow the user to control the irrigation and aspiration flow volumes, and by virtue of a specially designed catheter system, provide improved fluid flow parameters that facilitate quantitative volume exchange within a vessel or other cavity and produce defined fluid flow parameters in a region bordered by an occluding element. Accordingly, the aspiration and irrigation functions provided by the fluid exchange device can be added to several existing devices such as balloon occluding elements or filters, or can be used alone as a catheter-based fluid exchange system without any additional device. Thus, the fluid exchange capabilities can be added to an existing device such as a straight catheter or filter, or an existing device can be integrated into the remaining components of the present invention to provide the advantageous irrigation and aspiration functions as described herein. For example, to decrease time during a therapeutic or diagnostic procedure, the portion of the catheter element providing the irrigation function could be combined with a catheter used to perform an angioplasty procedure.

When so integrated, the irrigation and aspiration functions of the invention are located distal to the angioplasty balloon and the enhanced removal of emboli is facilitated. Also, the location of the irrigation and aspiration lumens can occur such that the aspiration ports are on opposite sides of an occluding member or other structure such that a direct irrigant to aspirant volume exchange may or may not occur in the lesion of a vessel. In preferred embodiments of the system of the invention, the catheter element provides turbulent, rather than laminar, flow within the vessel. Turbulence is introduced locally at the region of fluid exchange within the body. In a turbulent flow, the velocity at a point fluctuates at random with high frequency and mixing of the fluid is much more intense than in a laminar flow. Turbulent flow is specifically preferred because it reaches the walls of a body structure and facilitates both fluid exchange and dislodging of particulate matter. To reach the walls, the irrigation ports exit the catheter element in the direction of the wall. To accomplish this, the catheter element preferably has ports that exit orthogonal to the wall of the distal end of the irrigation lumen of the catheter. The aspiration lumen may establish a local laminar flow profile. This results in laminar flow about the vessel.

Also, in a turbulent flow, the velocity at a point fluctuates at random with high frequency and mixing of the fluid is much more intense than in a laminar flow. This is of particular value when attempting to clear any site of debris. Without turbulence, the flow along the sides of a vessel/lumen is approximately 0. When trying to remove/clear or exchange fluids thoroughly is it imperative to facilitate mixing. Mixing can only reach the vessel walls through the application of turbulence. This is appreciated by the vessels as well, since turbulence can be achieved with this invention without high-powered injection systems that carry physiological risks associated with their inherent power and abnormally high flow rates.

In more scientific terms, when a laminar flow is made turbulent, then the velocity will become more uniform and higher, and as a result, fluid particles in the boundary layer can move farther downstream before separation takes place. This turbulence is generally local to the irrigation area and controlled by the dimensions and orientation of the ports of the irrigation lumen.

The flow and velocity exchange rate through the entire system is not altered significantly since the turbulence is local area around the irrigation ports. But turbulence for an equivalent flow produces a much more uniform flow across the vessel. This results in higher velocities along the wall where emboli and thrombus are known to be in residence. From a physiological relevance standpoint, blood clots, or thrombi, are much more likely to be released into turbulent than in laminar flow. (Berne & Levy, 2001, *Cardiovascular Physiology*, p. 126).

Because flow is proportional to viscosity, irrigation with any number of fluids can increase the flow over just aspiration of the site. For example, the viscosity of blood is 5 times that of water in a vessel larger than 0.3 mm in diameter, (from graph 5–14, in Berne and Levy, p. 129). The resulting combination of turbulence and the introduction of various fluids allows for substantially variable fluid flows which cannot be achieved without the combination herein disclosed.

Those of skill in the art will appreciate that the fluid exchange capabilities and fluid flow parameters provided by the invention can be integrated into a number of systems to provide irrigation and aspiration and essentially any physiological context where near quantitative removal of fluid or particles from a site is desired. As noted above, the enhanced fluid flow parameters can be strategically oriented relative to the placement of an occluding member, such as a balloon, to effectively remove fluids or solid matter either proximal to or distal of the occluding device. The catheter element of the apparatus can also be positioned to facilitate the removal of dyes, or therapeutic or diagnostic compounds as part of the fluid exchange function of the apparatus of the invention.

In a preferred embodiment, the invention provides both irrigation and aspiration in a selected region of a vessel proximate to a lesion, but without any occlusion distal of the lesion such that the occluding element may be both inserted and removed without passing across the lesion. Because of the design of the catheter-based system, a single catheter element may both aspirate and irrigate and may be moved within the vessel whether or not used in combination with other apparatus. When used in combination with an occluding element, the irrigation and aspiration factors may be fixed in place proximate to a lesion within a vessel or may be movable such that a single catheter element having both aspiration and irrigation functions can be advanced into an area proximate a lesion and actuated to perform the irrigation and aspiration function both proximate to the lesion and distal to the occlusion element. Similarly, if there exists a distal device (filter or occlusion balloon) this system can be activated to accomplish the following optimum clinical benefit. The irrigation ports being just proximal, but not exclusively proximal, to the aspiration port, then the vessel can be irrigated actively with the local flow moving prograde. This drives the emboli up against a more distal occluder/filter and there the aspiration port evacuates the emboli. Used in concert with existing filters or balloons this results in optimum retrieval of emboli from the active irrigation. This embodiment does not require a proximal occlusion for clinical benefit.

In procedures where emboli may be present, this device may be used as part of a method to extract the emboli generated during either a therapeutic, surgical, imaging or diagnostic procedure. The volume exchange provided by the current invention is also adapted to facilitate removal of fluids within a measured portion of a vessel where vessel dimensions and fluid volumes are known. This device affords a simple mechanical means through which these may occur in concert. Primary applications have been identified that produce a 1:1 exchange of fluids, but further applications include pulsatile exchange rates and ratios other than 1:1.

The control aspect of the invention is derived in part from measured volumes that may be inserted and removed through a catheter system comprising an irrigation lumen and an aspiration lumen in fluid communication with irrigation and aspiration port(s) that insert and remove a defined or predetermined volume of solution. The design of the catheter and the fluid flow parameters achieved at the target site produce specific fluid dynamics within a vessel or body conduit that promote the removal of emboli and/or the near quantitative removal of a fluid contained in the region of a body conduit. In a preferred embodiment, a catheter coupled to a fluid exchange apparatus is actuated to create turbulence within the vessel or organ and proximate to the ports or exit holes of the irrigation lumen. As described in detail below, the size and orientation of the ports and lumen changes the fluid flow parameters such that defined flow rates, volumes, vortices, turbulence and ratios of fluids exchanged within the body can be custom designed for any application, vessel, or organ, as well as for specific diagnostic, therapeutic or imaging applications. Because many of the embodiments of the invention are used within the cardiovascular system, the irrigation and aspiration function can be designed such that fluids move into the vasculature in a pulsatile manner as with the movement of blood within the vessel caused by the beating heart. This type of fluid movement and fluid exchange provided by the aspiration and irrigation functions of the invention is advantageous because the insertion and removal of fluid in this manner exposes the vessels or other structures to fluid flow that is physiologically relevant. In the sense that the vessel experiences fluid flow that is similar to that experienced after the therapeutic, diagnostic, or imaging procedure is performed and any emboli that would be released following the procedure are more likely to be released during the irrigation or aspiration process performed by the devices of the invention.

As described in more detail below, the design also facilitates a defined fluid exchange rate, such as 1:1 volume exchange that avoids damage to the vessel while producing turbulence to facilitate the removal of emboli. Generally, turbulent flows provided by the device of the invention are localized and controlled in both volume and location and are typically higher than that provided by the existing devices in terms of both flow and velocity. Target flows of 1 cc/sec are relevant to vessels such as the vein grafts, flows up to 2 cc/sec are relevant for vessels such as the carotids. (Louagie et al., 1994, *Thorac Cardiovasc Surg* 42(3):175–81; Ascher et al., 2002, *J Vasc Surg* 35(3):439–44).

As noted above, an advantage of the invention is the generation of localized turbulence in the vicinity of the infusion catheter such that volume exchange within the vessel promotes the disruption of embolic particles that are only loosely attached to the interior walls of a vessel. This advantage is derived from both the design of the catheter, which affects the location in which fluids are inserted and removed into a vessel or an organ, as well as the specific design and function of the fluid exchange apparatus that, when coupled with the catheter of the invention, combine to produce improved fluid exchange and fluid flow parameters. For example, in an ordinary vessel that is roughly cylindrical within a defined axial distance along the length of a vessel, the removal of liquid generally produces a laminar flow through the center of the annular structure of the vessel and the fluid along the walls of the vessel are largely left in place. With a turbulent fluid flow profile, the fluid introduced into the vessel causes an exchange between the irrigant the existing fluid that is localized along the vessel walls and generally causes a more thorough mixing of the fluids within the vessel such that a more complete fluid volume exchange occurs and the removal of embolic particles is enhanced.

Although the particular parameters vary according to the designs described below, the fluid exchange achieved by the fluid exchange apparatus and the irrigation/aspiration catheter results in an insertion and removal of a defined volume within a vessel. As described in further detail below, the overall system is comprised of a fluid exchange apparatus that may have a mechanical or electrical, or both, fluid exchange component that converts a defined volume of fluid exchange with a defined axial movement of the catheter such that the volume of fluid exchanged per measure of distance of axial movement of the catheter through a vessel is known. Preferred embodiments of the fluid exchange apparatus are a substantially closed system wherein a reservoir containing irrigating fluid is combined with a reservoir containing the aspirated fluid such that known volumes are exchanged through a system that is essentially "closed" except for the exchange site within the vessel. The terms "substantially closed" mean that the system is closed because the volume of fluid inserted as irrigant solution is removed as aspirant solution in a predetermined ratio and any deviance from the ratio is attributed to only a volume of solution that is retained within the body at the target exchange site. For example, when a system of the invention is applied to irrigate and aspirate fluid from within a vessel, the system is substantially closed because the only difference between the fluid inserted as irrigant and removed as aspirant is that which is purposefully left behind in the vessel. When the volume exchange ratio of the device is set at a 1:1 ratio, the volumetric exchange of fluids is very near to equivalent. The fluid exchange apparatus may also be actuated in such a manner that the flow produced by actuating the fluid exchange apparatus is a defined increment. Thus, a known volume of fluid is exchanged at the target site and the clinician knows with certainty the volume of irrigant fluid that is inserted as well as the volume of fluid that is aspirated out of the target site.

In one embodiment, the device of the invention provides a 1:1 ratio of irrigation to aspiration fluid exchange such that the volume of fluid introduced to a vessel or organ is exactly matched by the volume removed. Through control of the location and movement of the device of the invention, the interior of a vessel or organ can undergo a complete fluid exchange by advancing the infusion catheter along the length of a vessel where removal of fluid is desired. By this process, several results are achieved that are beneficial therapeutically. First, the vessel experiences a turbulence and a fluid flow that is physiologically relevant in the sense that both the volume of fluid moving across a vessel as well as the turbulence are similar to the parameters that the vessel would experience under blood pressure. This similarity has several aspects. First, the turbulence that occurs in a vessel is similar to the turbulence caused by the motion of blood moved by a beating heart. Second, the pulsatile nature of the fluid exchange is also similar to the varying pressures and pressure profile caused by ventricular contraction and the ordinary movement of blood throughout the arterial system. Finally, these specific fluid flow characteristics are achieved without producing substantially increased pressures within a vessel and without distending the vessel through the application of increased fluid pressures. Thus, the combined irrigation and aspiration of controlled volumes of liquid treat the vessel with a physiologically relevant fluid profile.

Because the device of the invention offers the ability to introduce and remove a defined volume of fluid, the clinician can have a high degree of certainty that the entire internal volume of a region of a vessel has been rinsed with an irrigation fluid by knowing the approximate internal volume of the vessel and the length of the vessel in which irrigation and aspiration are performed. For example, assuming that a specified region of a vessel has an internal volume of 20 ml over a defined axial length. The device of the invention can be used to insert predetermined volumes of solution greater than, less than, or equal to 20 mls over the defined length of the vessel. Depending on the clinical environment, the ratio may be altered to remove greater volume by establishing a smaller ratio of irrigation to aspiration. One could, for example, irrigate with one volume of solution while removing twice the volume through the aspiration portion of the system to yield a 1:2 irrigation to aspiration volume.

In a preferred embodiment, the fluid exchange device has the ability to perform a controlled exchange of fluid with predetermined ratios including a 1:1 irrigation to aspiration ratio and varying ratios particularly values ranging between a 1:2 irrigation to aspiration ratio and a 2:1 irrigation to aspiration ratio. Preferably, this is achieved by having irrigant and aspirant reservoirs of defined volumes built into the fluid exchange device. However, the device can also feature a selectable control that alters the ratio of fluid exchange between a minimum and a maximum as a function of the operation of the device. In the mechanical embodiment of the fluid exchange device, each actuation of the device may cause a defined volume of fluid to be propelled through an outlet that is in fluid communication with the irrigant lumen of a catheter element. In combination, the device also features an aspirant reservoir which is expanded by a predetermined volume relative to the volume of the irrigant that is expelled.

The control of these parameters, in some aspects, by the fluid exchange device is the result of designing the fluid exchange device to cooperate with both conventional catheters as well as those specially designed to produce turbulent flow at the target fluid exchange site. The fluid control functions of the exchange device can also cooperate with the catheter element by incorporating the capability for the fluid exchange device to control motion of the catheter, specifically axial movement within a body conduit such as a blood vessel. In this embodiment, the catheter element is coupled to the actuation of the fluid exchange device by a coupled translation mechanism wherein, as described in further detail below, each actuation of the device results in automatic advancement or retraction of the catheter. Thus, a defined exchange of fluid volume at the target site occurs in combination with advancement or retraction of the aspiration and/or irrigation element of the catheter by a defined distance. In this manner, repeated actuation of the device provides a step-wise motion of the irrigation and evacuation functions and can insure a near quantitative volume exchange over a defined distance. As will be apparent from the following description, this aspect of the invention provides the ability to insert and/or remove a defined volume of fluid distal of an occluding member given an approximate knowledge of the dimensions of the vessel. As with the other embodiments, the operation of the system may provide fluid exchange with a pulsatile fluid flow by virtue of the application and dissipation of pressure achieved through the catheter.

Any number of designs for the fluid exchange apparatus can be used to provide controlled volumes of irrigation and aspiration fluids, through the catheter element of the invention to the target exchange site. The simplest embodiment of the invention provides a squeeze bulb wherein the irrigant and aspirant reservoirs are typically separated by a membrane and are in fluid communication with a irrigation and aspiration lumen that communicate fluids to and from the target site. In this embodiment, a one-way valve is provided preferably on both the irrigant and aspirant side of the fluid flow, to prevent aspirated fluid from flowing back to the target site. In another embodiment, a mechanical device causes pressure to be exerted on an irrigant reservoir that is in fluid communication with an irrigation lumen that provides fluid flow to at least one irrigation port at the distal end of a catheter. The catheter element also comprises an aspiration lumen, that may or may not be integral with the irrigation lumen, and which facilitates fluid communication of the aspirant fluid back to an aspirant reservoir. In this embodiment, the irrigant is expelled from a reservoir by the application of mechanical force to reduce the volume of the irrigation reservoir and the mechanical force is preferably coupled to an expansion of the volume of the aspirant reservoir to yield a defined fluid exchange between the irrigant reservoir and the aspirant reservoir.

Those skilled in the art of medical devices will appreciate that all of the component parts of the invention are assembled from biocompatible materials, typically medical plastics or stainless steel. The syringes described below may be ordinary medical-use syringes or may be custom fitted to be replaceable and to fit engagingly with the fluid exchange apparatus. An irrigant reservoir that is integral with the device may be pre-filled or a pre-filled syringe may be used to supply the irrigant fluid. In either a stainless steel or plastic embodiment, the device is stabilized. Typically, stainless steel devices are exposed to heat and steam in an autoclave, while medical plastics may be exposed to gamma irradiation or microbicidal gases such as EtO. The methods of the invention specifically include the use of any component of the system of the invention followed by sterilization of the components, or the entire system, and re-packaging for subsequent use. Although plastic embodiments are designed for single use, sterilization may be performed to functionally reconstruct the utility of the device after use with a patient.

In one preferred embodiment, a hand-held mechanical device is actuated by a trigger to insert and remove controlled volumes of fluid through the catheter element. The hand-held embodiment is comprised of an actuator such as a movable trigger that is mechanically operated by being grasped by the hand and pulled towards a stationary structural housing of a complementary portion of a housing to cause a reduction in the volume of an irrigant reservoir and, accordingly, fluid movement through an irrigation lumen and out one or more irrigation ports at the distal end of a catheter. Fluid provided to the target site in this manner is recovered through one or more aspiration ports and communicated through an aspiration lumen and returned to the aspirant reservoir of the fluid exchange device. The irrigant and/or aspirant fluids are preferably contained in a sealed reservoir system such as a cylindrical chamber having a piston and a rod wherein the piston is mechanically coupled to the actuating element. Motion of the actuating element transfers force to the piston and causes contraction of the irrigant reservoir and expulsion of liquid from the reservoir. Simultaneously, the motion of the actuator causes the expansion of the volume of the aspirant reservoir and causes withdrawal of fluid through the aspiration lumen and into an aspirant reservoir. In such an embodiment, the actuation of the trigger may translate into varying amounts of fluid flow depending on the mechanical expedients used. A single actuation of the trigger may translate into an incremental movement of a piston that exerts force on an irrigant and/or aspirant reservoir. By the use of several conventional mechanical apparatus, such as a ratchet and gear mechanism, a lever and pivot system, or others, the mechanical fluid exchange device exerts a direct control over the exchange of fluid communicated through the irrigation and aspiration lumens. The control of the fluid and the particular features can be provided in several designs that achieve the same function. For example, in addition to the hand-held apparatus described below, the force needed to create the fluid flow in both the aspiration and irrigation sides of the system could be provided by a mechanical foot pump, vacuum pump or virtually any component device that provides controllable fluid flow. Moreover, to provide total reproducibility in the operation of the system, a console controlled by a computer with appropriate commands or a software program is readily used to produce the same fluid flows, fluid exchange parameters, including exchange ratios, and essentially all of the functions of the purely mechanical embodiments described below. Therefore, those of ordinary skill in the art will appreciate that any number of mechanical or electrical variations give rise to the same fundamental principle wherein controlled volumes are applied to a target site through a segregated irrigation and aspiration system, preferably comprised of irrigation and aspiration lumens that pass through at least one catheter element and engage in fluid exchange at a target exchange site by virtue of specially designed irrigation and aspiration ports at the distal end of the catheter element.

By altering the dimensions of the irrigation reservoir and the aspiration reservoir, the ratio of fluid exchange between the irrigant and aspirant reservoirs is altered and, accordingly, the fluid exchange in the target vessel is adjusted. For example, where the irrigant reservoir and aspirant reservoir are of identical sizes, an actuation of the fluid exchange device may yield a 1:1 fluid exchange within the target vessel. Where, as described above, a different fluid exchange ratio is desired, the difference in the ratio may be achieved by a corresponding difference in the dimensions of the irrigant and aspirant reservoirs that are emptied and filled through the operation of the fluid exchange device. Also, variations in ratio may be accomplished by corresponding changes in the dimensions of in-line chambers as described below. Likewise, with a 1:1 ratio, equal volumes of irrigant and aspirant are exchanged in a single cycle of the fluid exchange apparatus. In the 1:1 embodiment, the entire irrigation and aspiration volumes may be exchanged within a defined number of cycles of the apparatus. For example, one may provide that each cycle of the hand-held apparatus provides 1 ml of irrigant volume and removes 1 ml of aspirant volume. By providing an irrigation and aspiration reservoir with known volumes, a known number of cycles translates into a known volume of irrigation and aspiration. As noted above, in one specific embodiment, the actuation of the device also causes translation of the infusion catheter along a defined axial path such that a known volume of solution is provided in both the irrigation and aspiration aspects as a function of the distance that is traveled by the infusion catheter.

Clearly, the irrigation reservoir may advantageously be divided into subparts and is not limited to ordinary aqueous solutions used in a surgical context. Given the utility of the present device for diagnostic and imaging applications, the irrigation reservoir could be filled with dyes, contrast agents, or other solutions that aid in the diagnosis or treatment of the vessel. Given that the fluid exchange device of the invention also provides unique fluid flow parameters, the irrigation reservoir could contain therapeutically valuable solutions such as heparinized ringers lactate, streptokinase, urokinase, tissue plasminogen activator, or other thrombus or emboli treatment fluids that are used to perform the therapeutic procedure on the internal portion of a vessel or organ. Given the ability to specifically tailor the fluid exchange parameters for a target vessel, the device offers the ability to use therapeutic compounds that might not otherwise be available because the clinician can be certain of the enhanced ability to remove solutions introduced via the irrigation reservoir. The fluid exchange apparatus can also be used to promote absorption of a therapeutic layer on a vessel wall. If a drug coated stent is produced that can reabsorb drugs after they have eluted, then with this device a high concentration of the drug can be introduced and pooled about the stent for a brief period. This high dose may then be absorbed or bonded back to the structure or one of its components and thereby recharging the drug coated stent.

Finally, in a system where it may be advantageous to have ratios other than 1:1 in the system it is also directly applicable. For example, in another vascular situation a virtual shunt may be created where a proximal fluid can be circulating and a fluid is infused distally. This would involve a ratio of greater than 1:1 irrigation to aspiration. Furthermore such an arrangement could introduce a second fluid to be the primarily distally delivered fluid. The second fluid could be blood, blood substitute, plasma or oxygenated fluid to produce a virtual shunt.

In the diagnostic use of optical coherence tomography, OCT, the fields of applications are presently limited by the need for a clear field. Similarly the use of intravascular ultrasound, IVUS, is somewhat limited by the attenuation associated with the blood in vivo. A substantial volume exchange of the vessel region in proximity of the distal end of the OCT or IVUS catheter would provide the opportunity to replace blood or other fluids with transparencies other than that found in blood, thus improving and/or modifying the imaging quality.

DESCRIPTION OF THE DRAWINGS

FIG. 2A is a section of the catheter showing the aspiration and irrigation lumens. FIG. 2B is insertion of the catheter element into an exchange region established at a terminal lumen characterized by a total occlusion such as a clot, lesion, abscess, a ball of wax or a body conduit or organ that is closed-ended such as an ear canal. FIG. 2C shows a cross-section of the system with an occlusion balloon to establish a defined region of fluid exchange between the irrigation lumen and the aspiration lumen. FIG. 2D shows one example of the placement of an aspiration port and an irrigation port that is in fluid communication with the aspiration lumen and irrigation lumen, respectively.

FIG. 3A is a catheter element having an occlusion member and comprising an occluding guiding catheter having an aspiration lumen and with the irrigation provided by a separate catheter to aid in defining a field of exchange. FIG. 3B shows a catheter element providing an isolated, localized region for fluid exchange that is maintained by irrigation occurring both proximal and distal to a centrally disposed aspiration port. FIG. 3C shows a typical laminar flow that fluids will naturally assume when passing through a cylindrical tube. The flow velocities are highest at the center of the tube and approach zero velocity at the walls of the tube. The length of the arrows indicate the magnitude of the velocity.

FIG. 3D shows the turbulent region of flow created by a catheter element of the invention adjacent to a region where the flow transitions to a laminar flow, but still has a comparatively higher velocity along the walls of the tube. At a distance from the irrigation ports, the flow achieves laminar flow.

FIG. 3E shows a catheter element with 3 rows of perfusion holes. The figure illustrates how the turbulent flow is most pronounced in the immediate vicinity of the infusion ports and begins to assume laminar characteristics until the next row of infusion ports is encountered. In the region designated "A," turbulent flow is provided by the irrigation port geometry. In region "B," flow is tending toward laminar flow. In region "C," laminar flow is established.

In FIG. 3F, the various regions of flow show the relative distances necessary for each activity. The transition region has typically been shown to be about the same length as the perforated region of the catheter element.

DETAILED DESCRIPTION OF THE INVENTION

The present invention may be used in a number of different environments and for a variety of purposes including, but not limited to all physiological uses of peristaltic or other pump for aspiration and irrigation including, IVUS, OCT, angioplasty, endortarectomy, cardiac stent placement, vessel treatment, diagnosis and repair, surgical placement of non-cardiac stents, insertion of pig-tail catheters, ear rinsers, etc. The following detailed description is exemplary of possible embodiments of the invention.

Figure 1:
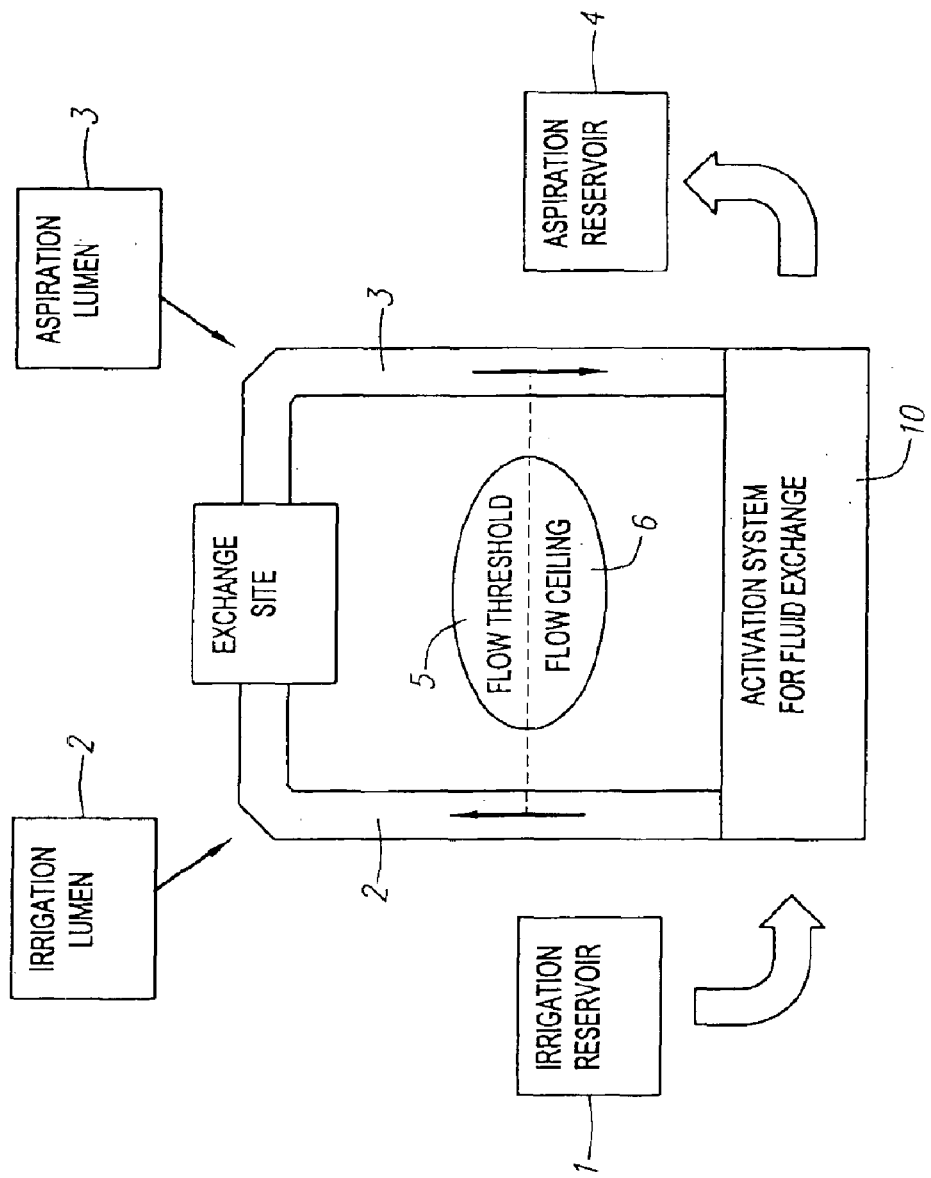
FIG. 1 shows the basic components of the device necessary for implementation with the optional inclusion of components that generate a minimum flow rate of exchange, components that incorporate an upper flow rate of exchange, and a configuration where a combination of flow threshold and ceiling provide a flow rate bandwidth.

Referring to FIG. 1, a schematic representation of the invention shows the basic components of the device necessary for implementation. The core fluid exchange or activation system maintains a substantially closed loop system with the target site for fluid exchange, e.g. the site within the body where aspiration and irrigation are applied. The irrigation component of the invention is conveniently provided by a dedicated irrigation reservoir 1, particularly when the fluid exchange system is the mechanical embodiment described in greater detail below. The exchange site is in fluid communication with the fluid exchange system via the irrigation lumen 2 and the aspiration lumen 3 which have exit or entry ports (not shown) at the distal end of each lumen. The aspiration component may also feature an aspiration reservoir 4 in fluid communication with the aspiration lumen 3 and aspiration ports (not shown) such that fluids removed from the exchange site are stored in the aspiration reservoir 4. As is apparent to one of ordinary skill in the art, the irrigation 1 and aspiration 4 reservoirs may be controlled electronically by valves or pumps to provide the controlled fluid exchange ratios described herein. Thus, while the embodiments of the invention featuring fluid exchange apparatus that are mechanically controlled by the user are preferred in certain versions of any system, controlled rate of fluid exchange at a target site may be used in a system of the invention. Alternatively, fluids in the aspiration reservoir 4 may be discarded. In one embodiment of the invention, fluids communicated from the target exchange site through the aspiration component of the invention are analyzed for chemical or particulate content to determine a level of removal of fluids or solid matter from the exchange site.

Referring again to FIG. 1, an optional configuration of the. components includes a flow valve 6 that produces a minimum lower threshold for irrigation flow. This minimum delivery flow is beneficial to ensure a minimum amount of exchange flow when the clinical indication dictates maintaining a minimum flow through the irrigation catheter. The flow threshold insures that the fluid exchange does not fall below a predetermined ratio as described herein. For example, although 1:1 fluid exchange rates are provided in several embodiments described herein, the exchange ratio may be altered such that a larger volume of fluid is aspirated compared to that which is used for irrigation or vice versa. Under such circumstances, the fluid exchange ratio would vary to, for example, a 1:2 irrigation to aspiration ratio under circumstances where a larger volume of liquid is desired to be removed from the exchange site.

The components of the invention could also incorporate an upper flow rate of exchange or flow ceiling 6. When conditions dictate that there is motivation to limit the velocity or overall flow parameters during a usage, a configuration that provides an upper limit may be provided. Accordingly, this embodiment would apply where a larger volume of fluid was desired to be inserted by irrigation compared to that which is removed by aspiration and the corresponding irrigation to aspiration exchange ratio would be increased to, for example, 2:1. The combination of a flow threshold and flow ceiling capability provide a flow rate bandwidth yielding a range of values between two extremes. In this embodiment, the exchange site can be irrigated and aspirated at a consistent level that is either fixed or varies within a range. This may also allow the activation system to sustain a change in the pressure level at the exchange site while delivering irrigant fluid or removing aspirant fluid at a steady rate or within a range of rates. As will be appreciated by one of ordinary skill in the art, the irrigation side of the system of the invention requires active force provided by the fluid exchange apparatus such that irrigant fluid flow is established at the target site. However, while the aspiration side may also be controlled through application of force to withdraw fluid from the target site, the aspiration side may also be passive such that the inherent pressure at the target site propels the aspirant fluid. The inherent pressure is typically provided both by the fluid pressure inside the body, e.g. the blood pressure within a vessel, and the pressure of the irrigant fluid entering the target site. This characteristically passive flow may be described as an efflux flow, see U.S. Pat. No. 4,921,478 which is specifically incorporated by reference herein. The passive flow of aspirant fluid is one way through the aspiration lumen and the fluid pathway is comprised of one-way valve, such as conventional duck bill valves having a minimal cracking pressure to allow passive fluid flow while preventing retrograde flow through the aspiration side of the system. This capability provides for constant extraction of embolic particles throughout a clinical procedure while irrigant fluid flow is maintained and/or when fluid existing at the target site flows from endogenous body pressure.

Figure 2A:
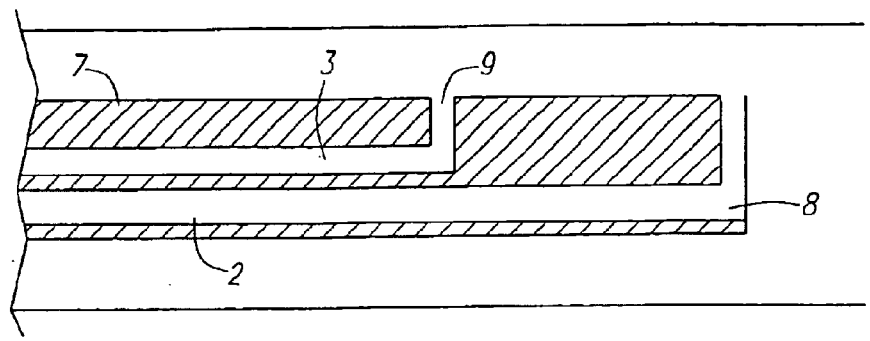
FIGS. 2A–2D are cross-sections of a vessel showing the catheter element of the invention with aspiration and irrigation lumens combined in the same catheter element and terminating at an aspiration and irrigation port, respectively.
Figure 2B:
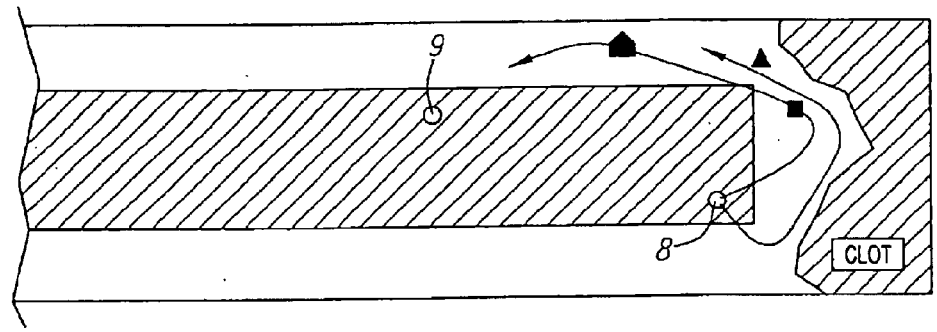

FIG. 2A is a cross-section of a catheter element 7 of the invention at the exchange site. The irrigation lumen 2 in this configuration terminates at or proximate to the distal end of the catheter element. While the aspiration lumen 3 termi-nates proximally and both lumens terminate with exit ports 8,9. FIG. 2B depicts the insertion of fluid into an exchange region at a terminal lumen. The irrigation port 6 in this depiction is dislodging a terminal occluding clot. The terminal occlusion may include but is not limited to a clot, lesion, abscess, a ball of wax or an ear canal. In such situations, simple aspiration may not eliminate the lesion and a non-traumatic irrigation of the lesion with a therapeutic formulation, in concert with aspiration after an improved treatment methodology. For example, even if the irrigation fluid is able to produce a substantial breakdown of a terminal occlusion, the occlusion itself must still be cleared. Moreover, the combination of irrigation and aspiration to yield fluid exchange after the ability to introduce pharmaceutical agents proximate to the occlusion and the ability to remove the agents before they enter the bloodstream. A specific example of this is a thrombolytic agent used to remove the occlusion or potentially dangerous thrombus, wherein the thrombus or occlusion must be both treated and removed to treat the condition and wherein the necessary dosage of the agent exceeds that which could otherwise be introduced without drug-related toxicity.

Figure 2C:
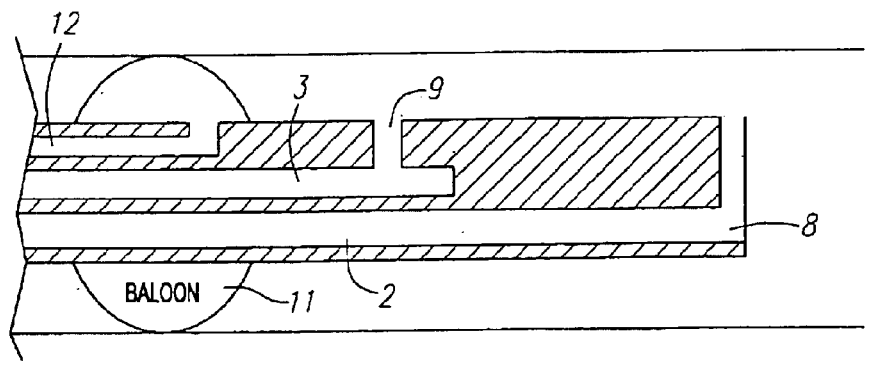
Figure 2D:
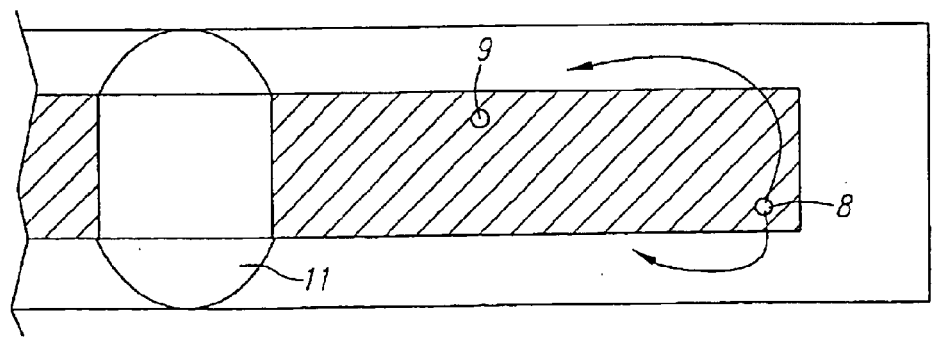

FIG. 2C is a cross-section of the catheter element of the system incorporated with a proximal occlusion balloon 11 to establish a defined region of fluid exchange. This configuration may be useful for, but is not limited to, occluding flow, limiting a diagnostic agents field of deployment or limiting the bodies exposure to a high intensity agent. A dedicated balloon lumen 12 is provided for inflation of the occluding device. FIG. 2D is the catheter element of the system of the invention having an occlusion member 11 to aid in establishing an exchange site and having irrigation and aspiration functions distal to the occluding member wherein the arrows depict the general direction of fluid flow, distal to proximal, relative to the occluding member 11.

Figure 3A:
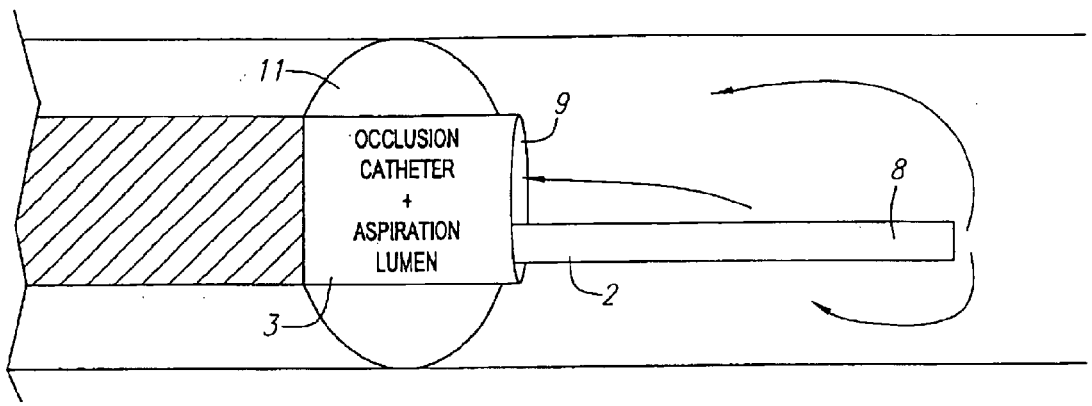
FIGS. 3A–3F show the catheter element in various configurations and illustrate the difference between laminar and turbulent flow.
Figure 3B:
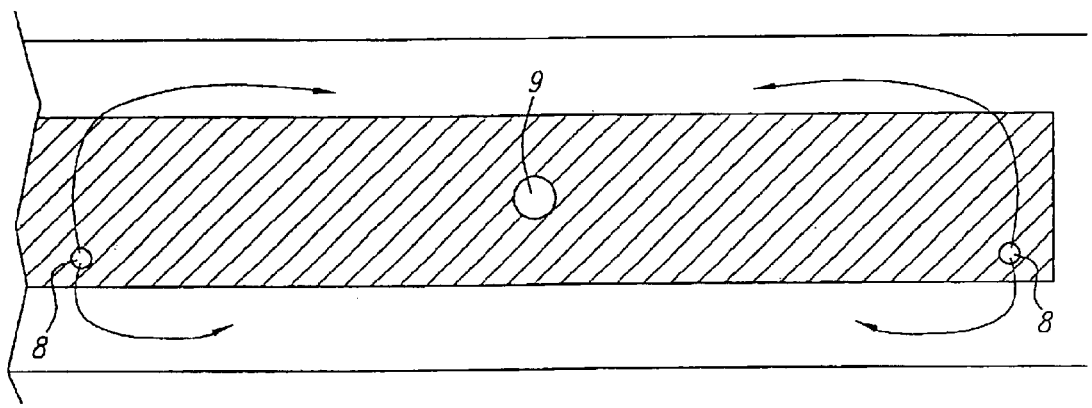
Figure 3C:
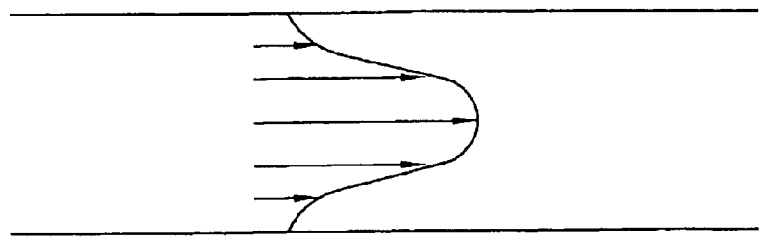
Figure 3D:
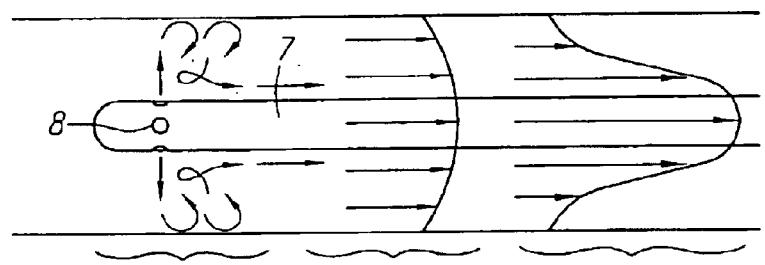
Figure 3E:
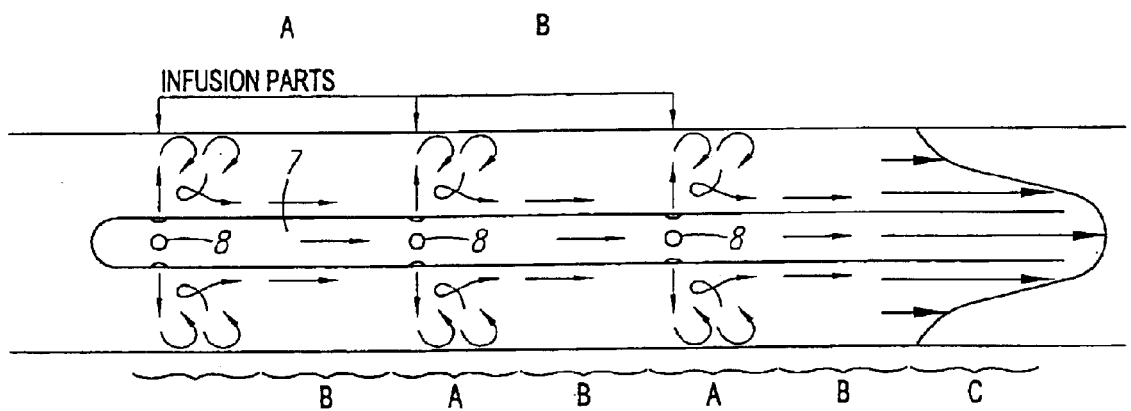
Figure 3F:
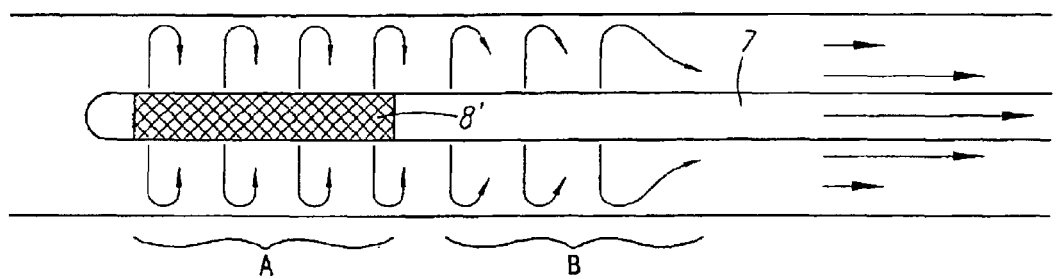

FIG. 3A is the device incorporated with a combined aspiration lumen 3 and occluding element 11 integral in the same catheter element with the irrigation driven by a separate catheter 2 to aid in defining a target site or field of fluid exchange. The irrigation lumen's 2 independent travel affords a means of adjusting the location of the fluid exchange site while maintaining the occlusion at a predetermined location. Furthermore, a treatment, diagnostic or imaging tool (not shown) can also be affixed to the irrigation catheter 2. This is productive where the resident fluids are desired to be replaced with a dye or contract agent and then removed in turn prior to re-establishing normal blood flow. In optical coherence tomography (OCT), for example, it is advantageous to introduce and remove a low attenuating fluid. FIG. 3B is a fluid isolated region that is maintained by irrigation occurring through ports 8 located both proximal and distal to the aspiration port 9. This configuration presents a means of maintaining a controlled introduced field of fluid between the proximal and distal irrigation ports 8. As in the embodiment of FIG. 3A, a treatment, diagnostic or imaging tool could be attached or moved along in concert between the irrigation ports. Referring to FIG. 3C, a catheter element (not shown) that merely inserts and removes fluid from a vessel achieves only laminar flow in the direction of the arrows and with velocity illustrated by the size of the arrows. Near the vessel wall the total fluid flow approaches zero such that fluid containing emboli at the walls is not disturbed and loosely affixed emboli remain in place. FIG. 3D is a preferred embodiment of the catheter element of the invention having orthogonally disposed aspiration ports 8 located at the distal end of the catheter element 7. The region "A" experiences turbulent flow, while region "B" experiences a flow profile that is in transition from turbulence to laminar flow. FIG. 3E shows a series of irrigation ports 8 spaced at intervals along the length of the distal end of a catheter 7 such that either turbulent flows, designated as "A" or regions where turbulence is transitioning to laminar flows, designated as "B" are established along a length of the catheter 7 to substantially eliminate areas of laminar flow. FIG. 3F shows a configuration wherein the irrigation ports are provided as a perforated region 8' at the distal end of the catheter 7. The arrows indicate the direction and magnitude of flow showing that the perforated region establishes turbulence in a defined region, and as the distance away from the perforated portion 81 increases, the flow reverts to a laminar flow at a certain distance along the length of the vessel.

Figure 4A:
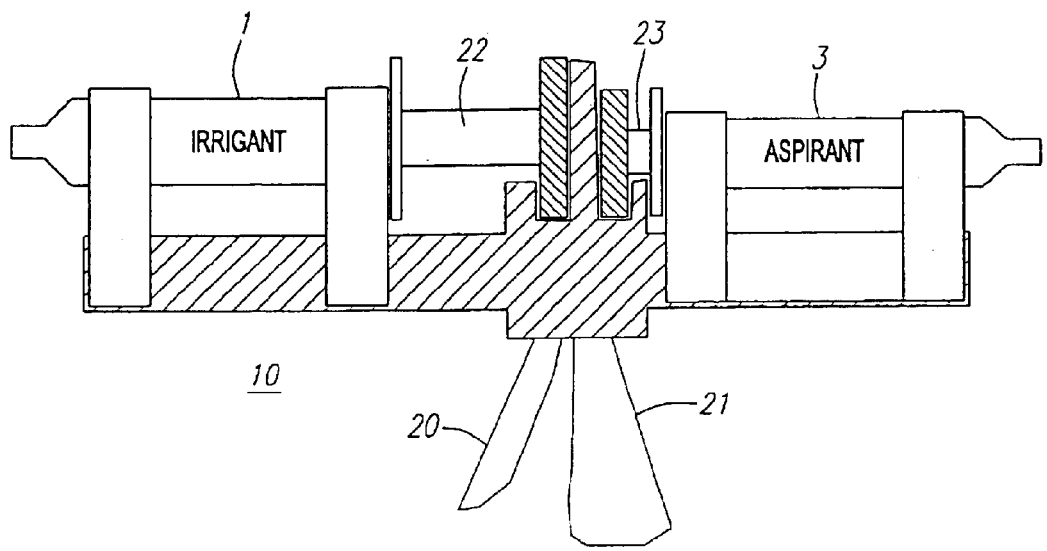
FIG. 4A is a schematic of an embodiment of the fluid exchange device that produces pulsatile flow through the application of leverage to a hand-held unit that is actuated to communicate force to the irrigant reservoir and which collects fluid in the aspirant reservoir.

FIG. 4A is an embodiment of the device 10 that produces pulsatile flow through the application of a mechanical force to an apparatus that propels fluid through the catheter element of the invention. In use, the action of a trigger 20 pulled toward a handle 21 exerts a force on a dedicated irrigant piston 22 that compresses the irrigant reservoir 1 thereby reducing the volume of the irrigant reservoir 1 and forcing fluid through the irrigant lumen (not shown) and simultaneously withdraws the dedicated aspirant 23 piston of the aspirant reservoir 4 to accomplish the fluid exchange at the target site. Actuation of the trigger 20 may cause the relative motion of the pistons 22, 23 by connection handle to a ratchet or other gear mechanism that provides the exertion of force in an incremental amount based on the actuation of the handle in a cyclical fashion. See e.g. FIG. 10 below and accompanying text. As shown in FIG. 4A, the irrigant and aspirant reservoirs may advantageously be provided by conventional syringes or similar devices that provide for fluid containment and the controlled application of fluid flow. The syringes of FIG. 4A are merely examples of the use of replaceable cartridges that may be readily inserted and removed from the device. Such cartridges are particularly useful when pharmaceutically active solutions are pre-filled and used in specific clinical procedures where medicaments are provided to a body conduit or vessel by the system of this invention. In this respect, the use of this invention allows the selective introduction of pharmaceutical compositions of any type during the performance of an ordinary irrigation and aspiration operation. In the embodiment of FIG. 4A, the syringes comprising the irrigant reservoir 1 and aspirant reservoir 3 may be removably inserted into the hand-held fluid exchange apparatus 10 and used to both provide and expel a predetermined volume of fluid through the target exchange site. In this manner, both the volume and content of the irrigant fluid can be controlled by exchanging syringes and the contents of the aspirant reservoir can be retained and analyzed for fluid or particular content. The operation of preferred embodiments of the hand-held embodiment of the invention is also described at FIGS. 7–10 below and the accompanying text.

Figure 4B:
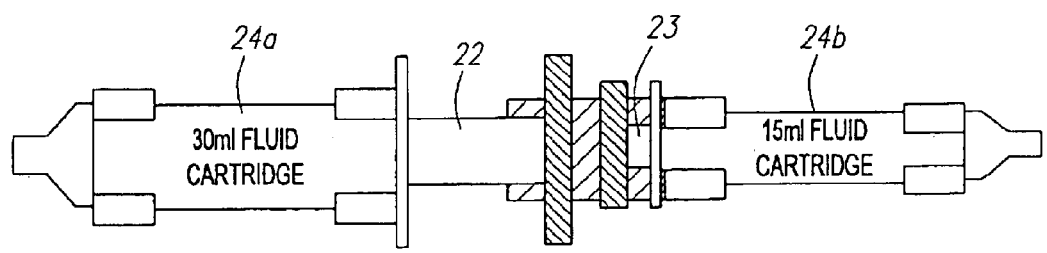
FIG. 4B is an embodiment that accepts interchangeable fluid cartridges, similar to syringes, for irrigation and aspiration and where the exchange rates can be altered to other than a 1:1 ratio. In this example there is a 2:1 ratio of irrigant to aspirant dictated by the relative sizes of the fluid cartridges.

FIG. 4B is an example of interchangeable fluid cartridges 24a 24b, similar to the syringes described in other embodiments, for irrigation and aspiration. As described in greater detail herein, the irrigant 1 and/or aspirant 3 fluid reservoirs may be provided by cartridges or reservoirs of differing sizes to accomplish the predetermined volume exchange ratio desired for the particular clinical indication. In the embodiment of FIG. 4B, the irrigant fluid cartridge 24a has double the volume of the aspirant cartridge 24b thereby providing a 2:1 fluid exchange ratio of irrigant to aspirant at the target site. In this respect, the loop established by the fluid exchange system is not a completely closed loop, but is described as a substantially closed loop, in that a difference exists between the volume expelled through the irrigant reservoir 1 via the irrigant lumen 2 and into the exchange site versus the difference in the aspirant volume taken up through the aspirant lumen and into the aspirant reservoir 40 although the volumes are not identical, the volumes are predetermined and known with certainty as is the volume of fluid that remains at the target site, which is the difference between the volume of the irrigant fluid introduced to the site and the volume of the aspirant fluid removed therefrom. As in the embodiment of FIG. 4A, the irrigant fluid cartridge 24a has a dedicated piston 22 for expelling fluid from the cartridge. The aspirant cartridge 24b similarly has a dedicated piston 23 for collecting fluid introduced to the aspirant reservoir via the aspiration lumen 3. In this specific embodiment, more irrigant fluid is introduced due to the larger cross-section of the irrigant cartridge 24a while the overall length of the cartridge that fits into the fluid exchange apparatus remains constant. This technique for providing varying fluid cartridge volumes is advantageous when the irrigant and aspirant cartridges are replaceable in a fluid exchange device.

Figure 5A:
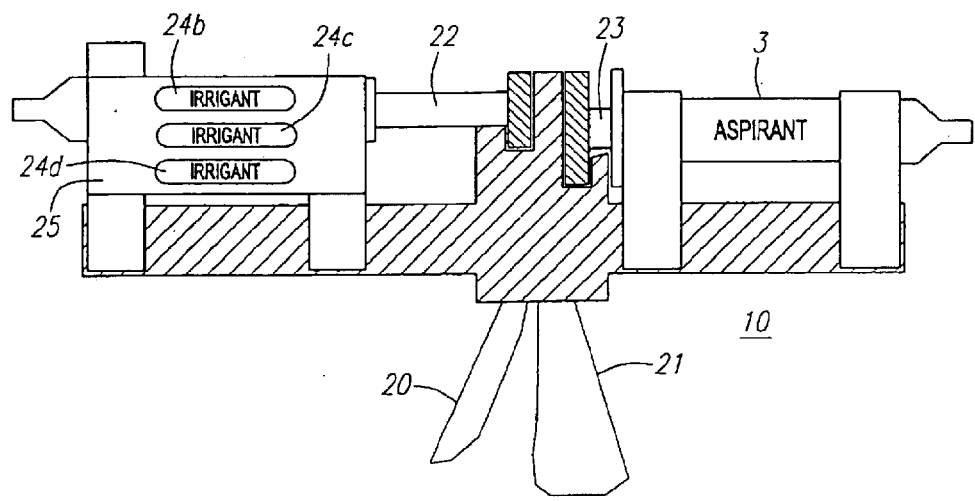
FIG. 5A is a fluid exchange device incorporating a segregate irrigant reservoir that uses different types of irrigants, while FIG. 5B segregates the irrigant fluid into a sample to be inserted both proximal to and distal at a point of the target site.

FIG. 5A is a revolving cartridge 25 that can rapidly provide a series of irrigant solutions. This revolver-style orientation of irrigant solution is advantageous for delivery of a sequence of different fluids or for delivery of a pharmaceutical composition at an intermediate point during a procedure. In use, the revolving cartridge 25 is oriented such that the series of irrigant fluids 24b, 24c, 24d are positioned in line with the dedicated irrigant reservoir piston 22 to expel the selected irrigant solution placed in line with the piston 22. Under certain clinical circumstances, the application of the system of the invention may provide an ordinary rinsing solution such as saline at the beginning of a procedure to clear resident fluids and/or emboli from a site, followed by the introduction of a pharmaceutical solution, followed by the removal of the pharmaceutical solution and the subsequent introduction of a neutral solution. In such a use, the saline solution would be confined in the first irrigant reservoir 24b, which would be infused by actuating the handle 20 as in the embodiment of FIG. 4A described above. Subsequently, the contents of the second irrigant reservoir 24c, such as a thrombolytic agent, dye, contrast agent or other formulation, is inserted by rotating irrigant reservoir 24c in line with the irrigant reservoir piston 22, and similar actuation of trigger 20. Once the desired effect provided by the solution of reservoir 24c has been achieved, the solution may be rinsed from the vessel by rotating the dedicated irrigant reservoir 24d into place and actuating the fluid exchange system as above. Similarly, a variety of aspirant chambers (not shown) can be used to facilitate collection and testing of the aspirant fluid by segregating discrete volumes into containers that can be processed for analysis.

Figure 5B:
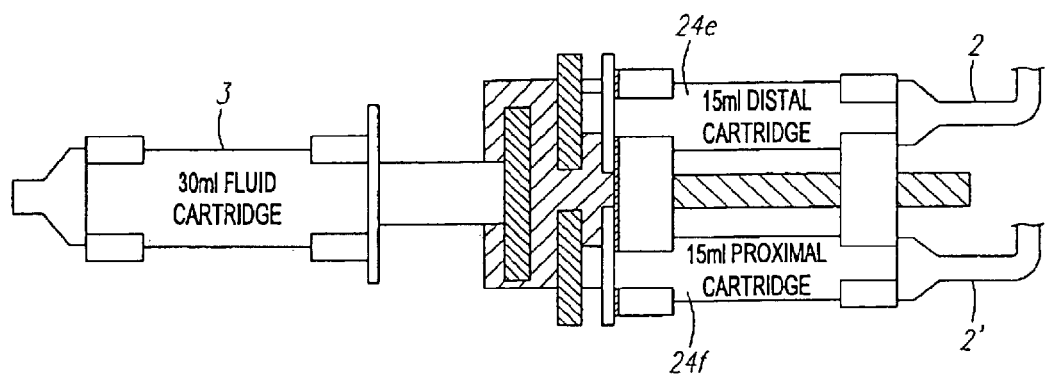

FIG. 5B is an embodiment where two different irrigant fluids can be delivered at equal time and measure in a pair of cartridges 243, 24f that are designed to be delivered through one or a pair of irrigant lumens 2, 2' such that one irrigant lumen 2 delivers fluid distal to a predetermined point at the target site and the other irrigant lumen 2' delivers fluid proximal to a predetermined point at the target site. In such a case, each of the two irrigant lumens 2, 2' has a dedicated irrigant port or ports located at the distal end of the catheter element. The division of the irrigant reservoir 1 into two components 24e, 24f allows for the selective introduction of irrigant fluids, which may be the same solutions or different solutions at two or more points within the target site. The predetermined point in the target site that separates the proximal and distal delivery of irrigant fluid may be an aspirant port located therebetween (as in the embodiment of FIG. 2D) or any other structure where separation of irrigant fluid is desired. For example, some irrigants may mix advantageously only at the exchange site and could not be combined outside the body based on their chemical reactivity.

Figure 6:
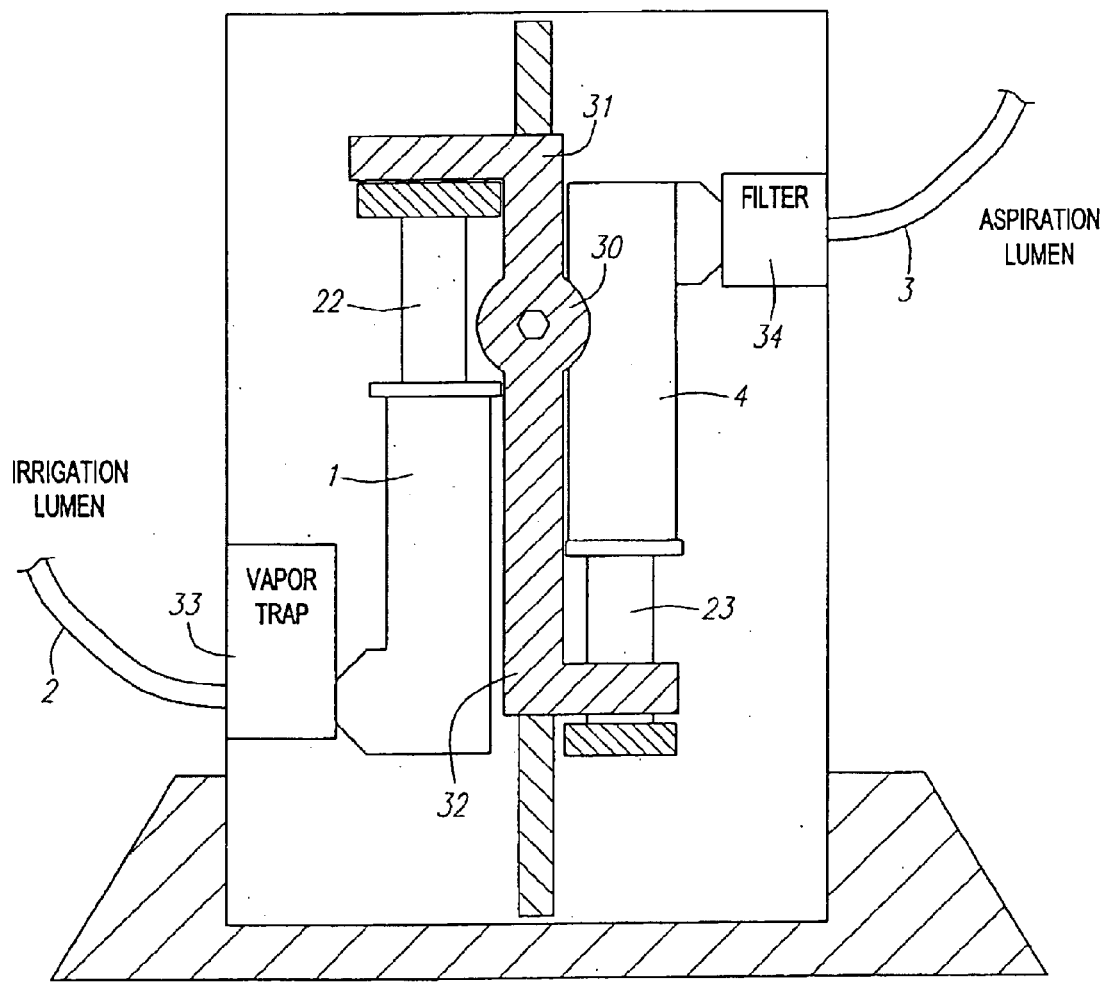
FIG. 6 is a tabletop version of the fluid exchange device that is suitable for either a mechanically drive hand system or an electronically controlled, pump-driven system, including an optional in-line air trap for the irrigant and a filter for the aspirant.

FIG. 6 is a tabletop version of the fluid exchange device of the invention. As is described elsewhere herein, the fluid exchange apparatus of the invention may be controlled by the simple mechanical operation of a device by a user or by an electronic system that controls a mechanical or electrical pump- or valve-driven system to control the irrigant 1 and aspirant 4 reservoirs. In the embodiment of FIG. 6, a variable position lever 30 drives the stroke of a dedicated piston 22, 23 that forces fluid from the irrigant reservoir and draws fluid into the aspirant reservoir. As with the embodiments described above, the cycle and the volume of the reservoirs or motion of the pistons can be altered to match the fluid exchange volume needed for any flow in the vessel or body conduit. Because the rotation of the individual levers is variable, the ratio of fluid exchange can be achieved by different positioning of the lever arms 31, 32 rather than by altering the volume of the individual irrigant 1 and aspirant 4 reservoirs. Although this embodiment shows the mechanical application of force through levers, a tabletop version of the apparatus of the invention is advantageous when electronically controlled pumps are provided to control the fluid exchange and fluid exchange ratios. The embodiment of FIG. 6 also may include an in-line air trap 33 for the irrigant reservoir 1 and/or a filter 34 for the aspirant reservoir 4. As it may be advantageous to eliminate debris upon extraction of irrigant fluid and/or prevent air upon entry of irrigant fluid, the inclusion of a filter or trap 33, 34 for air and/or emboli is appropriate in some cases.

Figure 7A:
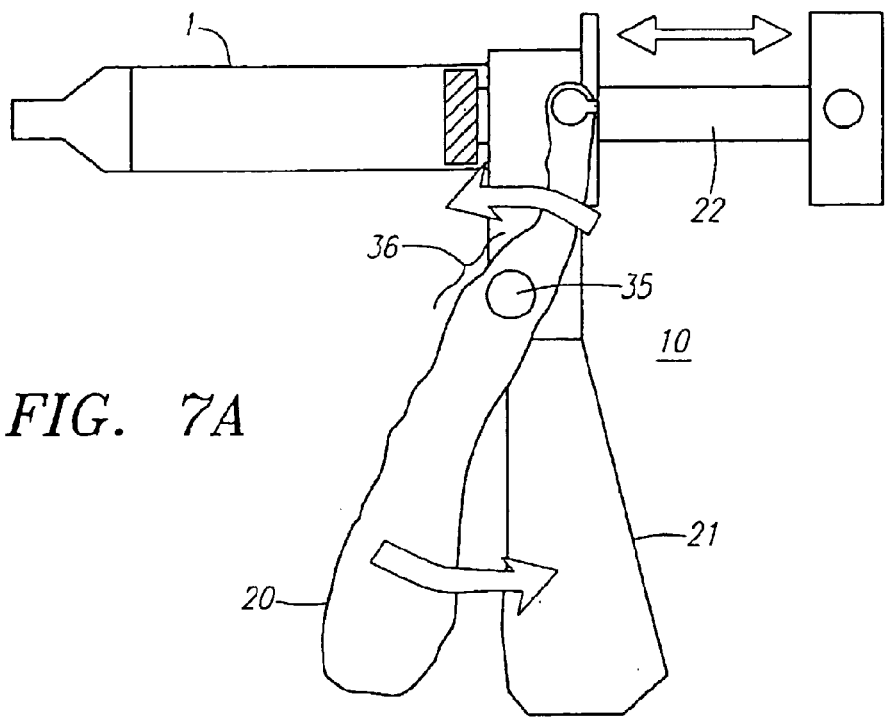
FIGS. 7A and 7B are a grip lever activated embodiment of the hand-held fluid exchange device of the invention wherein the actuation of a trigger relative to the body of the handle translates into the motion of a piston that propels fluid from the irrigant chamber and collects fluid in an aspiration chamber (not shown).
Figure 7B:
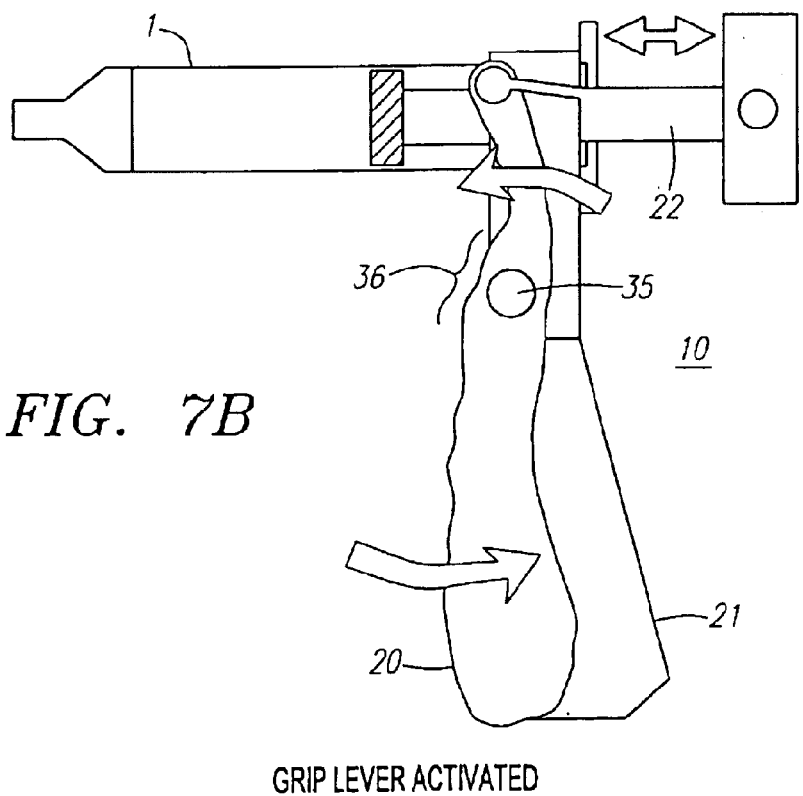

FIGS. 7A and 7B show the internal structure and function of a fluid exchange device 40 where a pair of reservoirs control fluid flow via the force exerted by pistons or plungers following the action of a trigger 20 and handle 21 connected to or integral with a lever 36 that rotates about a pivot 35. In this embodiment, the actuation of the trigger 20 rotates the level 36 about pivot 35 and forces the irrigant reservoir piston 22 into the irrigant reservoir 1 and simultaneously withdraws the aspirant reservoir piston 23 out of the aspirant reservoir. From the relaxed position (FIG. 7A), the trigger 20 can be activated to drive the pistons 22, 23 through either a direct coupling or a mechanism for incremental cycles. If desired, the trigger 20 can return to the relaxed position after a cycle from spring action in the handle or pivot 35 other automatic return mechanism. The reservoirs may be integral to the device 10 or the volume of the reservoir 1 may be attached to a separate reservoir (not shown) together with the appropriate lumens, and preferably in-line one-way valves, to facilitate the exchange between the separate reservoir and the chamber of the device. In the former embodiment, the reservoirs are integral to the handle-operated device such that the piston exerts a direct force on the irrigant 1 and/or aspirant 4 reservoir to exert the force necessary for fluid exchange. In the above embodiment, the internal structure of the device acts as an in-line chamber that is intermediate between the separate reservoir and the lumen such that irrigant fluid residing in a separate reservoir is drawn into the chamber prior to being expelled from the chamber through the irrigation lumen. In this embodiment, a pair of lumens are required, a first intermediate lumen connecting the separate reservoir to the chamber, and a second lumen communicating the irrigant fluid from the chamber through the irrigant lumen and via the irrigant ports to the target exchange site.

Figure 8:
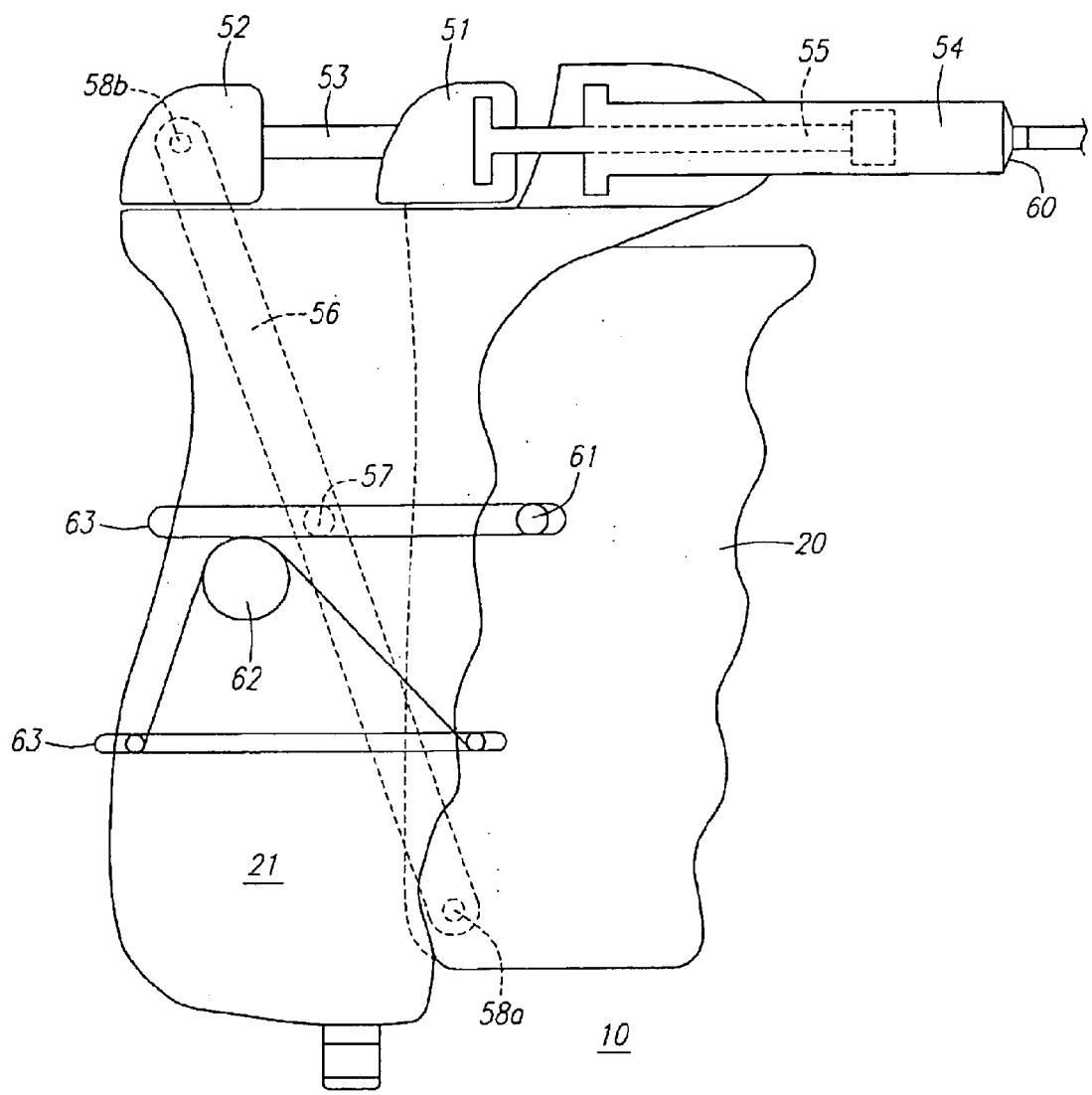
FIG. 8 is a preferred embodiment of the hand-held fluid exchange apparatus of the invention having a spring tensioned trigger mechanism that is actuated by manual motion of the trigger relative to the body of a handle. Actuation causes linear or incremental motion of a dedicated irrigant and aspirant carriage that move in opposite directions to control the force supplied to the irrigant and aspirant reservoir, respectively.

FIG. 8 is a preferred embodiment of the invention having a trigger 20 that is squeezed by the hand to operate a syringe that acts as the aspirant reservoir 54 and the irrigant reservoir (not shown). As the trigger 20 moves toward the body of the handle 21, the force is transmitted both to the piston 55 dedicated to the aspirant reservoir 54 and a separate piston (not shown) dedicated to the irrigant reservoir. Although the internal configurations can be varied to incorporate other mechanical expedients, the orientation of the lever 56 and pivot 62 of the present embodiment provide an advantageous mechanism for a 1:1 ratio fluid exchange. The action of trigger 20 is communicated to a lever 56 that is connected to the trigger 20 by a first terminal lever connector 58a. When the trigger 20 moves toward the body of the handle 21, the force exerted on the lever 56 rotates the lever 56 around pivot 57 to exert a force, via a second terminal lever connector 58b that is attached to an irrigant carriage 52. Simultaneously, the motion of the trigger 20 exerts force on a second lever (not shown) that is connected to the aspirant carriage 51 in a similar matter as for the irrigant carriage 52. The motion of the trigger 20 provides a simultaneous but opposite force on the aspirant cartridge 51 compared to the irrigant cartridge 52. The simultaneous forces that are applied to the pistons dedicated to the irrigant reservoir and aspirant reservoir 54, respectively, occur in opposite directions to yield a substantially equivalent volume exchange into the aspirant reservoir 4 and out of the irrigant reservoir 1 via the aspirant and irrigant lumens 4, 2 respectively. The motion of the irrigant carriage 52 is translated to the piston dedicated to the irrigant reservoir by virtue of a connector 53 that is noncompressible and that is aligned with the length of the irrigant reservoir 1.

As noted specifically with the embodiments described at FIG. 4A herein, the irrigant and aspirant reservoirs 1, 4 may be interchangeable syringes or cartridges that can be inserted and removed to introduce specific solutions or fluid volumes. In a preferred embodiment, the irrigant and aspirant reservoir 1, 4 may be molded into the body of the device such that the fluid volumes for the irrigant and aspirant reservoirs are separately filled via a fixture that acts as an input valve to the irrigant and/or aspirant reservoir. The irrigant and aspirant reservoirs 1, 4 preferably have removable fixtures at the output 60 thereof for attachment of the respective lumens 2, 3.

The motion of the trigger 20 is rendered linear and reproducible by slots 61 cut into a portion of the trigger 20 that are engaged by the first pivot 57 and the second pivot 61 such that the body of the handle 21 and/or the trigger 20 slidingly move about either of the pivot structures. A second lever 63 operates parallel to the lever 56 to enable the trigger 20 to travel smoothly along its path. This configuration provides for reproducible motion of the trigger 20 relative to the body of the housing 21 and also facilitates attachment of a spring 62 that biases the trigger in the forward position so that actuation of the trigger 20 relative to the handle 21 produces a complete cycle that translates into a defined movement of both the irrigant cartridge 52 and the aspirant cartridge 51. The volume exchange ratio provided by the device of this invention may be altered by changing the relative lengths of the lever 56 relative to the pivot 57 or by altering a ratcheting mechanism disposed at the connection point between the lever 56 and the irrigant cartridge 52 such that a complete cycle of the trigger 20 from the forward most position when moved toward the body of the handle 21 constitutes a complete cycle that moves the irrigant 52 and/or aspirant cartridge by fixed distance. The spring tension automatically returns the trigger 20 to the forward most position to prepare for a second cycle.

Figure 9A:
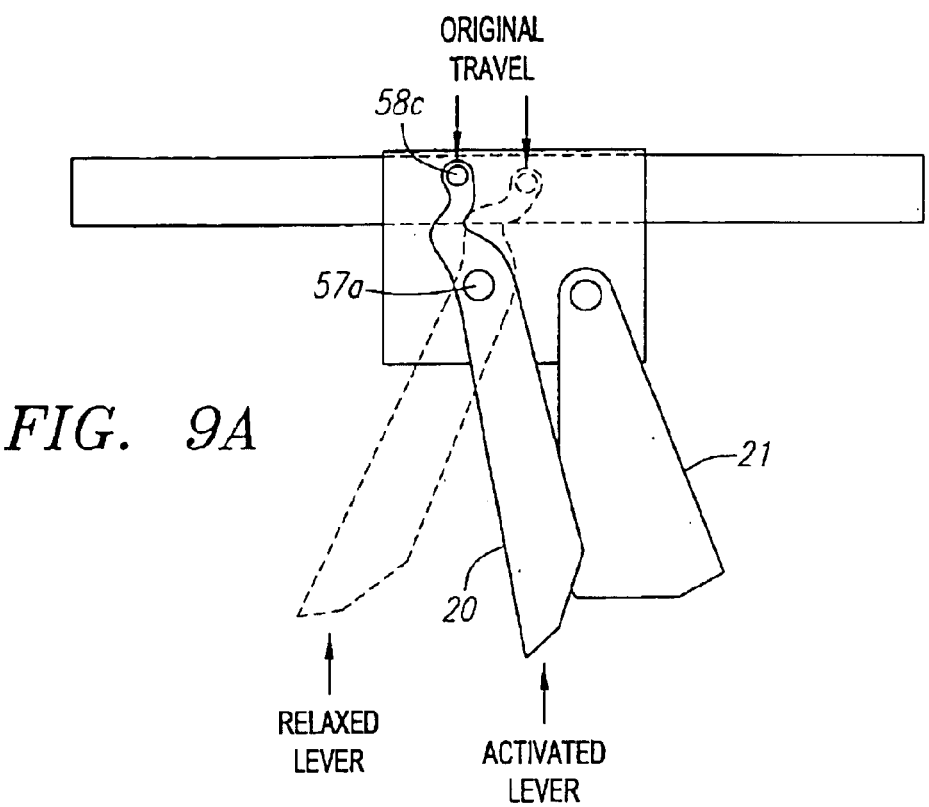
FIGS. 9A and 9B illustrate an embodiment at the hand-held fluid exchange device having an adjustable pivot point on a trigger to produce different flow rates and peak pressures.
Figure 9B:
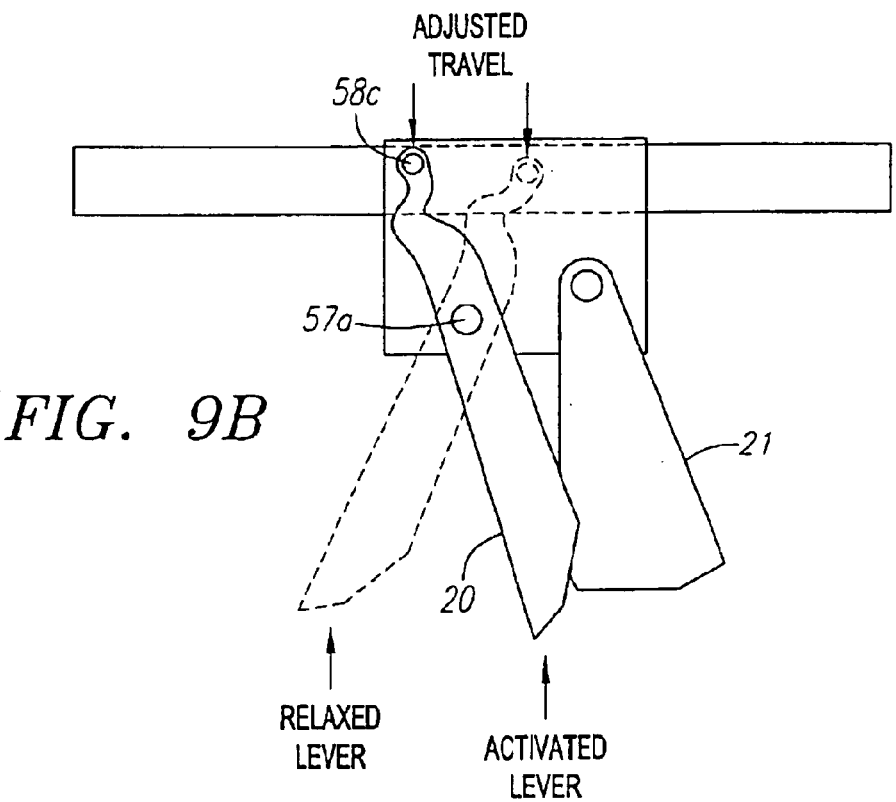

FIG. 9A is an embodiment where the travel of the lever in the fluid exchange device is adjustable so that the amount of fluid displaced in a single cycle can be controlled, and both the distance traveled and the force generated can be adjusted by relative positions of the trigger 20 and the handle body 21. The embodiments of FIGS. 9A and 9B illustrate the ability to alter the fluid flow parameters of the fluid exchange device by changing the configuration of the mechanical components that exert force on the irrigant reservoir 1 and aspirant reservoir 4, respectively. FIG. 9B illustrates the adjustment of the pivot point 57a to produce different flow ratios and peak pressures based on the relative position of the pivot point 57a about which the trigger 20 rotates. In such an embodiment, if more fluid flow is desired the apparatus can be easily adjusted to accomplish a variable number of flows for a given grip cycle. The travel distance provided by the motion of the trigger 20 as exerted at the point of attachment by the second terminal lever connector 58c dictates the amount of fluid flow expelled from the irrigant and/or aspirant reservoir 1, 4 based on the action by a syringe or aspirant reservoir piston or carriage as described above. Accordingly, an increase in the motion of a piston compressing fluid in an irrigant or aspirant reservoir or chamber, due to changing the pivot point, results in an increased exchange rate for a given activation of the trigger 20. As is shown in FIGS. 9A and 9B, the adjustment to the degree of travel of the trigger 20 relative to the handle 21, when combined with aspiration 51 and irrigant 52 carriages and reservoirs as described in, for example FIG. 8 above, produces the variable fluid flow of this embodiment. As with the embodiments described above, the mechanical movement of the trigger 20 relative to the handle 21 is translated into fluid flow from an irrigant reservoir 1, via irrigation lumen 2, aspiration lumen 3, and aspirant reservoir 4 by the configurations described herein.

Figure 10:
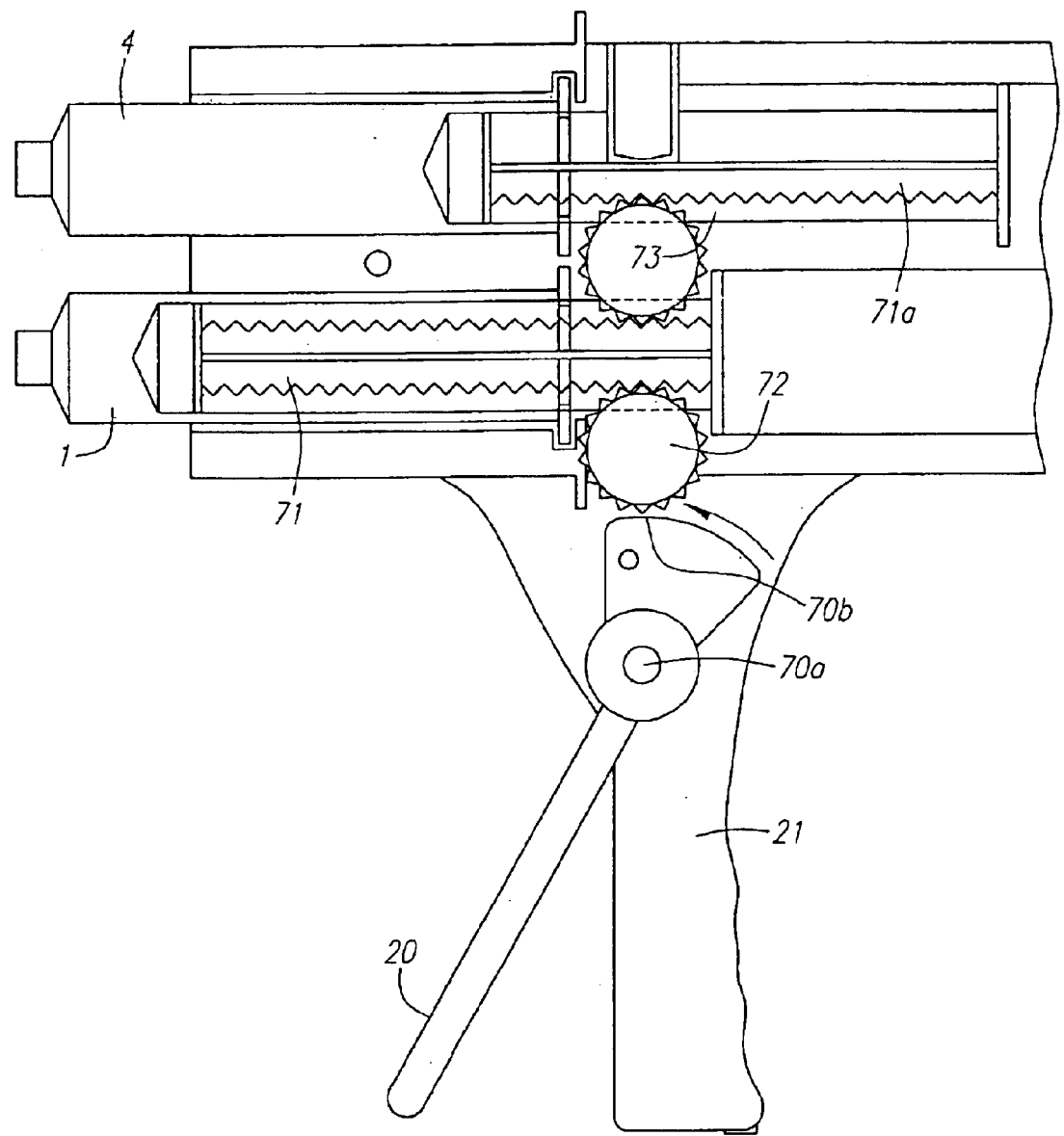
FIG. 10 is an embodiment wherein the control of the movement of pistons that propel fluid from a cylindrical irrigant reservoir and into an aspirant reservoir is provided by a ratchet mechanism.

FIG. 10 is a hand-held fluid exchange apparatus of the invention wherein a ratchet mechanism provides for incremental movement of a piston, in this embodiment, a general set of pistons 71, 71a for driving fluid out of the irrigant reservoir 1 and into the aspirant reservoir 4, respectively. As in the embodiment of FIG. 8, the motion of a trigger 20 relative to a body handle 21 completes one cycle. This embodiment may also contain a mechanical or electrical counter that provides a readout indicating the number of cycles that have been performed, the volume of fluid introduced or removed, or the amount of fluid present, or remaining in either reservoir. In this embodiment, the motion of the dedicated, geared piston 71 in the irrigant reservoir 1 is controlled by the ratchet mechanism which is comprised of the trigger 20, a pivot 70, about which the trigger 20 rotates, and gear 70b that engages a first ratchet wheel 77. Preferably, the ratchet mechanism is one-way such that motion of the trigger 20 toward the body handle 21 rotates the first ratchet wheel 72 that rotates to advance or contract the piston 71. In the example of FIG. 10, actuation of the trigger 20 about pivot 70a translates to rotation of the first ratchet wheel 72 via gear 70b. The rotation of the first ratchet wheel 72 is translated to the geared piston 71 and this rotation is in turn translated to a second ratchet wheel 73 that rotates in the opposite direction to the first ratchet wheel 72 that is in turn connected to a geared piston 71a in the other reservoir.

In the embodiment of FIG. 10, the device is designed to be hand-operated such that the manual actuation of the trigger 20 causes automatic motion of the two ratchet wheels 72, 73 and the geared pistons 71. The equivalent dimensions of the reservoirs 1, 4, pistons 71, 71a, and the two ratchet wheels 72, 73 shown in FIG. 10 yields an approximate 1:1 fluid exchange ratio. In addition to altering the dimensions of the aspirant 4 or irrigant 1 reservoirs, the alteration of the fluid exchange ratio can be achieved by altering the dimensions of the ratchet wheels 72, 73.

Figure 11:
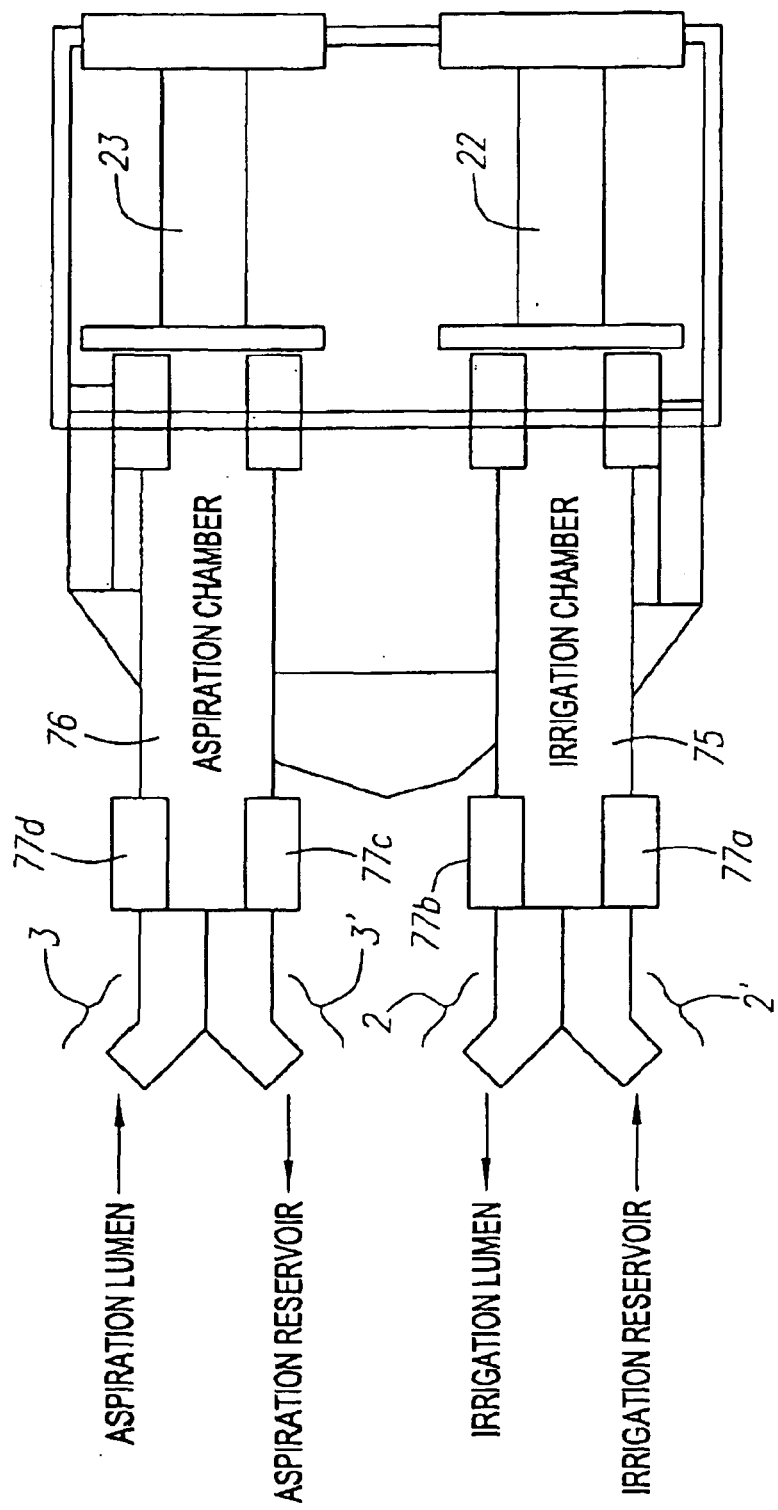
FIG. 11 is a fluid exchange device with two chambers, such that both an irrigation and aspiration chamber are arranged to operate in concert, with one filling and one expelling fluid in each direction and having separate input and output pathways for connecting to the reservoir and lumen elements.

FIG. 11 shows the principles of a fluid exchange device with a segregated irrigant 75 and aspirant chambers 76 each having a dedicated inflow and outflow line. In this embodiment, the inflow line of the irrigation chamber 75 is an irrigation inflow line 2' that communicates fluid held in the irrigation reservoir 1 to the irrigation chamber 75. The fluid is drawn into irrigation chamber 75 by the dedicated piston 22 and is subsequently expelled through the irrigation lumen 2 into the target site for fluid exchange as described previously. Similarly, fluid is drawn from the target site through the aspiration lumen 3 and into the aspiration chamber 76 by operation of the dedicated piston 23 whose motion both pulls fluid through the aspiration lumen 3 and into the aspiration chamber 76, but also expels fluid from the aspiration chamber 76 to the aspiration reservoir 3, via the aspiration reservoir outflow line 3'. This embodiment of the invention operates much like a two-stroke engine wherein fluid is pulled into the irrigation 76 and aspiration 75 chambers and. subsequently expelled through the appropriate lumen. To control the flow of fluids, each of the dedicated inflow and outflow lines for each chamber have valves 77a, b, c, d that control the fluid flow. For example, when fluid is drawn into the irrigation chamber 75, a valve 77a on the chamber inflow line 2' is opened while the piston 22 is pulled back. Subsequently, the inflow valve 77a closes and an outflow valve 77b that is in line with the irrigation lumen is opened while the irrigation chamber piston 22 is forced into the irrigation chamber 75 to expel fluids through the irrigation lumen 2. Similarly, when the action of the aspiration chamber piston 23 is used to draw out fluid into the aspiration chamber 70 via aspiration lumen 3, an inflow valve 77d on the aspiration chamber inflow line 3 is opened and the in-line valve 77b in the aspiration chamber outflow line 3' is closed. To expel fluid from the aspiration chamber 76 through the outflow line 3' and into the aspiration reservoir 4, the in-line valve 77d on the aspiration lumen 3 is closed and the in-line valve 77c on the aspiration reservoir outflow line 3' is opened. As for the embodiments described above, the action of the individual pistons 22 and 23 used to cause the fluid flow throughout the system can be controlled manually by mechanical expedients affixed to the pistons. Alternatively, electronic circuitry can control the speed motion and cycle parameters of both pistons such that the fluid flow is electronically controlled according to a user interface or a predetermined fluid exchange profile. As will be apparent to one of skill in the art, the cycling action of this embodiment produces a pulsatile flow with the relative motion of both pistons 22, 23. Moreover, the particular minimum and maximum pressures in each pulsatile flow can be controlled by the relative action of the pistons 22, 23.

In another embodiment, the in-line valves are not actively controlled, but are provided as simple one-way valves that only allow fluid inflow from the irrigation 1 reservoir into the irrigation chamber 75 and, likewise only allow fluid outflow from the irrigation chamber 75 through the irrigation lumen 2. On the aspiration side of the system, one-way valves allow fluid flow only from the aspiration. lumen 3 to the aspiration chamber 76, and from the chamber 76 to the aspiration reservoir 4. In use, when the device is activated, the piston plunger in either chamber will produce a positive flow through the lumen. When the lever begins to relax, the one-way valve will close and the irrigation reservoir 1 will fill the chamber. On the aspiration side, one-way valves on both the lumen 3 and the reservoir 4 ensures that the aspirant fluid is purged into the reservoir and, during relaxation, the aspirant is extracted from the exchange site via the aspiration lumen 3. Actuation of the pistons simultaneously causes simultaneous fluid flow to and from the target site while a ½ cycle out of phase yields a transient pressure increase within the system.

Figure 12A:
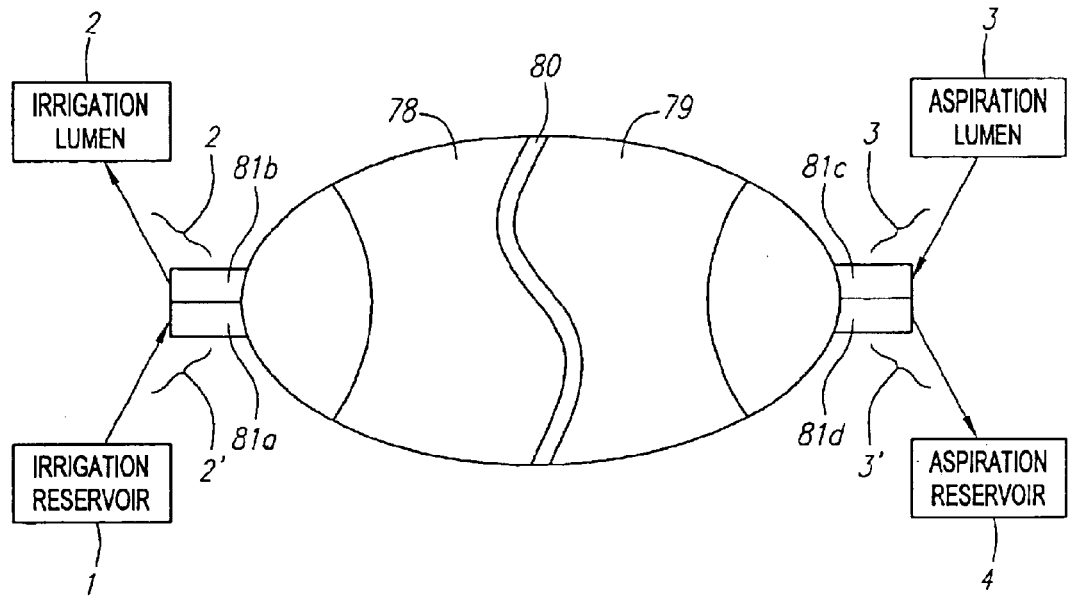
FIGS. 12A and 12B show the apparatus configured as a compressible ball squeezed by the hand with the internal volume divided into irrigant and aspirant chambers and designed to be connected in-line with irrigation and aspiration lumens and reservoirs.
Figure 12B:
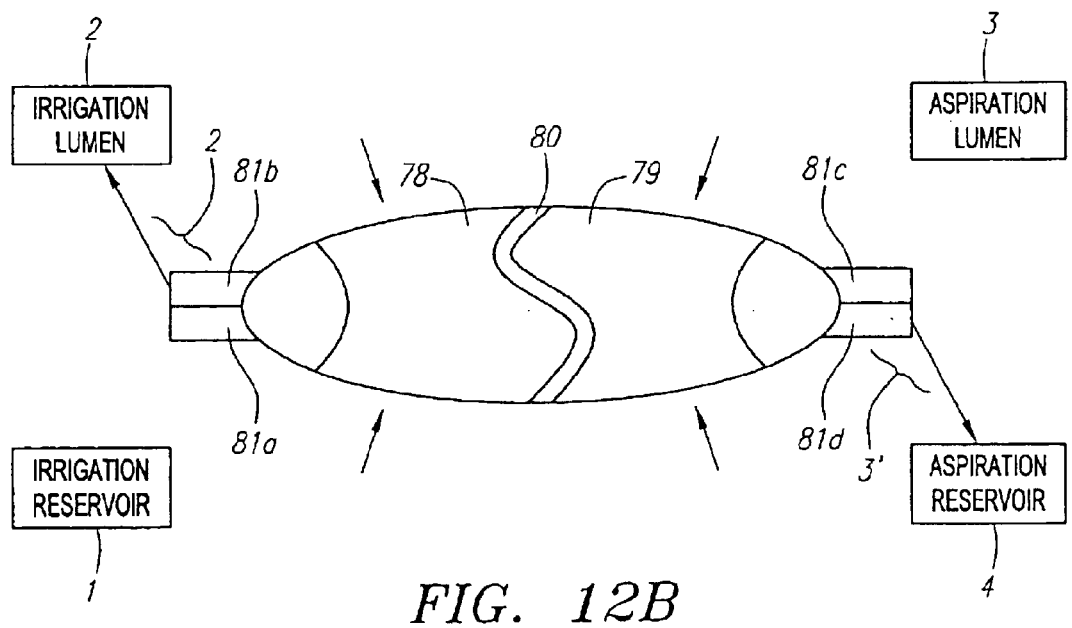

FIGS. 12A and 12B show a hand-held fluid exchange apparatus configured as a compressible handball with the internal volume divided into irrigant and aspirant aspirant chambers 78, 79 in series with dedicated inflow and outflow lines connecting irrigation 1 and aspiration 4 reservoirs, respectively. With a fluid impermeable wall disposed between the irrigant 78 and aspirant 79 chambers, the collapse of the ball under force will circulate the fluids appropriately. Referring to FIG. 12A, the apparatus is divided into an irrigation chamber 78 and an aspiration chamber 79 by a fluid impermeable barrier 80 that completely segregates the two chambers 78, 79 within the device. The expansion and contraction of the irrigant chamber 78 causes fluid flow through a dedicated inflow line 2' between the irrigation reservoir 1 and the irrigant chamber 78 and out to the target exchange site via the irrigation lumen 2 and terminates at the target site as in the other embodiments described herein. Similarly, aspirant fluid is drawn in through the aspiration lumen 3 into the aspiration chamber 79 and out through the dedicated aspiration chamber outflow line 3' and into the aspiration reservoir 4. As in the embodiment of FIG. 11, one-way flow valves are advantageously disposed in each inflow and outflow line between the lumen and chamber, and chamber and reservoir. Thus, a one-way flow valve 81a allows fluid flow only in the direction from the irrigation reservoir, via inflow line 2', into the irrigation chamber 78. The fluid inside the irrigation chamber 78 may only flow in the direction through one-way valve 81b and out through the irrigation lumen 2. Aspiration fluid entering aspiration chamber 79 via aspiration lumen 3 may enter only in the direction through one-way valve 81c and aspiration fluid inside the aspiration chamber 79 may pass only in the direction of the aspiration reservoir 4 through one-way valve 81d.

Referring to FIG. 12B, pressure exerted on the compressible structure of the device, as indicated by the bold arrows in FIG. 12B, compresses both irrigant chamber 78 and aspirant chamber 79 such that fluid flows in the direction of the arrows i.e. irrigant fluid flows through one-way valve 81b, through irrigation lumen 2 and to the target exchange site. Aspirant fluid flows from the aspiration chamber 79 through the one-way valve 81d and into the aspiration reservoir 4. Fluid flow is prevented by one-way valves 81c and 81a from entering either the aspiration lumen 3 or the irrigation reservoir 1. Upon relaxation, the outer surface of the handball moves in a direction opposite to the bold arrows in FIG. 12B and the flow is reversed. Thus, fluid flows from the irrigation reservoir 1 through the one-way valve 81a and into the irrigation chamber 78. Likewise, fluid flows from the aspiration lumen 3, through one-way valve 81c, and into the aspiration chamber 79. This configuration is similar to the embodiment of FIG. 11 because a chamber 78 or 79 is provided at an intermediate position between the exchange site and the reservoir such that a volume of fluid is held at an intermediate position between each reservoir 78, 79 and the exchange site for purposes of exerting control over a discrete volume of fluid separate from the irrigation and aspiration reservoirs 1, 4.

Figure 13A:
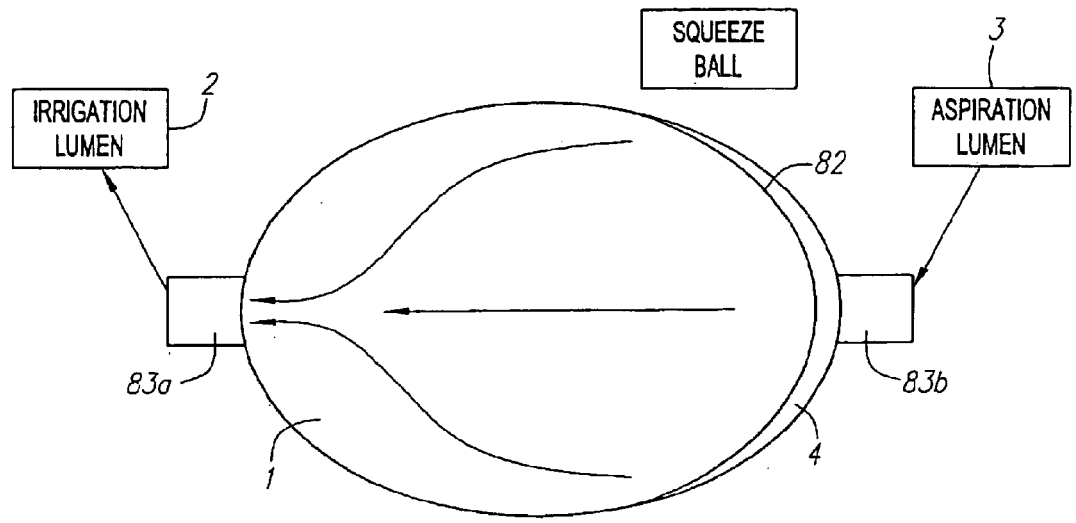
FIGS. 13A and 13B are an embodiment wherein the fluid exchange device is a hand ball pump configured with an internal reservoir of irrigant fluid and a flexible member to separate the irrigant from in-flowing aspirant fluid. This device is initially loaded with a volume of irrigant that encompasses most of the initial internal volume of the ball and which flows through the target site to the internal aspirant reservoir.
Figure 13B:
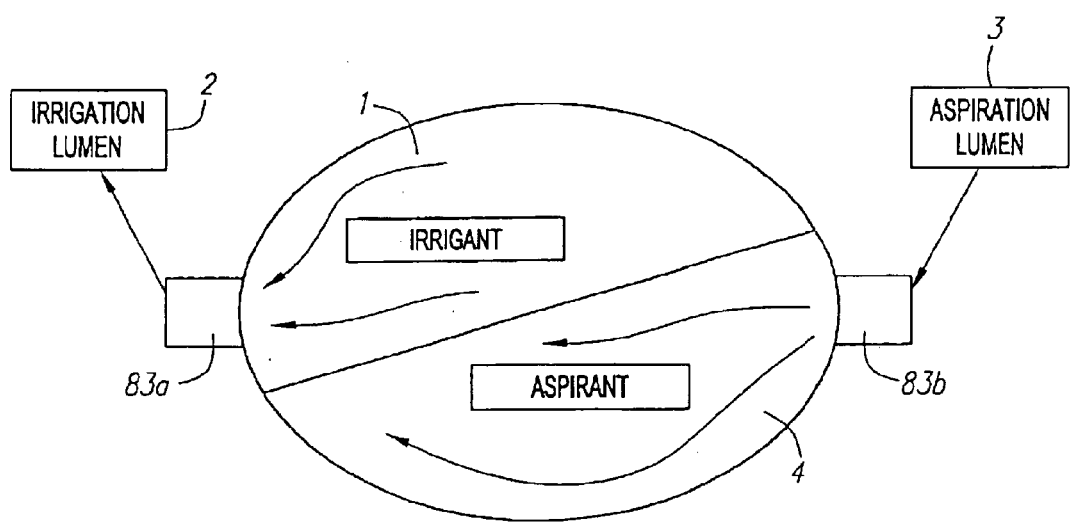

However, the compressible handball configuration can be constructed to allow direct manipulation of the irrigation reservoir 1 to expel fluid while simultaneously collecting aspirant fluid within the discrete structure of the handball itself. FIGS. 13A and 13B show a handball pump configured with an internal reservoir of irrigant and a flexible barrier 82 to separate the irrigant and aspirant reservoirs 1, 4, which are disposed inside the handball. Referring to the embodiment of FIG. 13A, prior to connection of this embodiment of the invention to a catheter element, the irrigant reservoir 1 is preferably filled with fluid to substantially encompass the entire internal volume of the handball. The flexible and fluid impermeable barrier 82 deforms towards the outer wall of the handball to accept irrigant solution and to simultaneously minimize the internal volume of the aspirant reservoir 4. When used in a clinical setting, the irrigant reservoir 1 is filled with the pharmaceutically acceptable composition to be used as the irrigant and the apparatus is sealed and may be sterilized while intact. Before using, the device is connected to the irrigation lumen 2 and aspiration lumen 3 which may be filled with fluid to establish the substantially closed loop as described previously. As in the embodiment of FIGS. 12A and 12B, one-way valves 83a, 83b are positioned in-line between the irrigation reservoir 1 and the irrigation lumen 2, and between the aspiration lumen 3 and the aspirant reservoir 4. As the handball is compressed, fluid flow generally occurs in the area of the arrows to force fluid out of the irrigant reservoir 1, through the irrigation lumen 2 and into the target site while any backflow is prevented by the one-way valve 83a. Accordingly, aspiration fluid is drawn through the aspiration lumen 3 and collects in the aspirant reservoir 4. FIG. 13B shows an embodiment of the invention wherein approximately half of the irrigant solution has been expelled through the irrigation lumen 2, exchanged at the target site, and collected back in the aspirant reservoir 4 via aspiration lumen 3. As above, fluid flow generally occurs in the direction of the arrows as the internal irrigant volume is exchanged between the irrigant reservoir 1 and the aspirant reservoir 4.

Figure 13C:
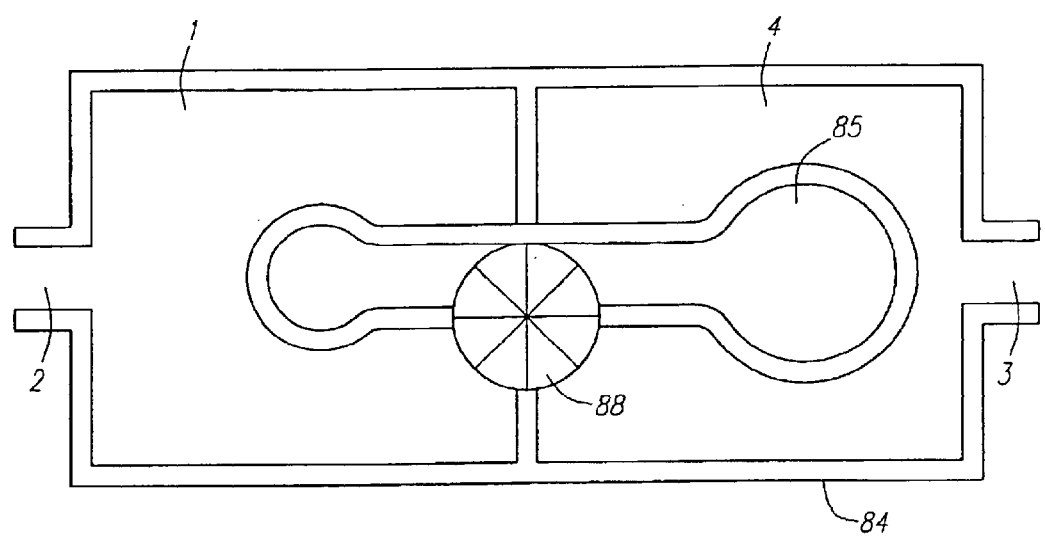
FIG. 13C is an embodiment having a substantially rigid external housing and an internal balloon. The interior of the housing is filled with fluid and an internal balloon containing air or a non-volatile gas. A volumetric pump changes the internal configuration of the balloon to force fluid from an internal irrigant reservoir to an internal aspirant reservoir.

As noted above, the principal of the invention may be achieved by both user operated, generally mechanically controlled embodiments of the invention, or through electronically controlled apparatus that usually require electronically controlled pumps and/or valves. In the embodiment of FIG. 13C, a volume metric pump 86 with an internal balloon 85 is provided to achieve the fluid exchange function of the invention. Generally, the device is comprised of a housing 84 that is preferably substantially rigid and which contains an internal irrigant reservoir 1 and aspirant reservoir 4 connected to dedicated irrigation and aspiration lumens 2, 3, as described previously. Volumetric control is achieved by selectively expanding an internal balloon 85 within the housing 84 to be positioned in either the irrigant reservoir 1 or aspiration reservoir 4. As with the embodiments of FIG. 13A and 13B, at a preliminary point in the use of the device the irrigant reservoir 1 is generally full and the internal volume balloon 85 is confined in the aspirant reservoir such that the internal volume of the balloon 85 is maximized within the aspiration reservoir 4 and does not displace a substantial volume of the irrigant reservoir 1. This allows the maximum amount of irrigation fluid to exist within the irrigant reservoir 1 prior to use of the device. As the fluid exchange process occurs, the volumetric pump 86 functions by forcing a portion of the internal volume of the balloon 85 into the irrigant reservoir 1. The volumetric pump 86 may be controlled by the user or through an electrical circuitry that provides an output reading to dictate the volumes or relative percentage volumes between the reservoirs 1, 4. As the volume exchange process continues, the internal volume of the balloon 85 is transferred to a greater and greater degree from the aspirant reservoir 4 to the irrigant reservoir 1 to displace the internal volume of the irrigation fluid. At a half-way point, the internal volume of the balloon is equally disposed between the two reservoirs (assuming that the beginning volume of the two reservoirs is equal) and the volumes of the fluid contained in both the irrigant 1 and aspirant 4 reservoirs is equal. As described previously, a simple modification of the dimensions of the apparatus allow variation of the volume exchange ratio from a 1:1 value to any prescribed ratio dictated by the clinical circumstances.

Figure 14:
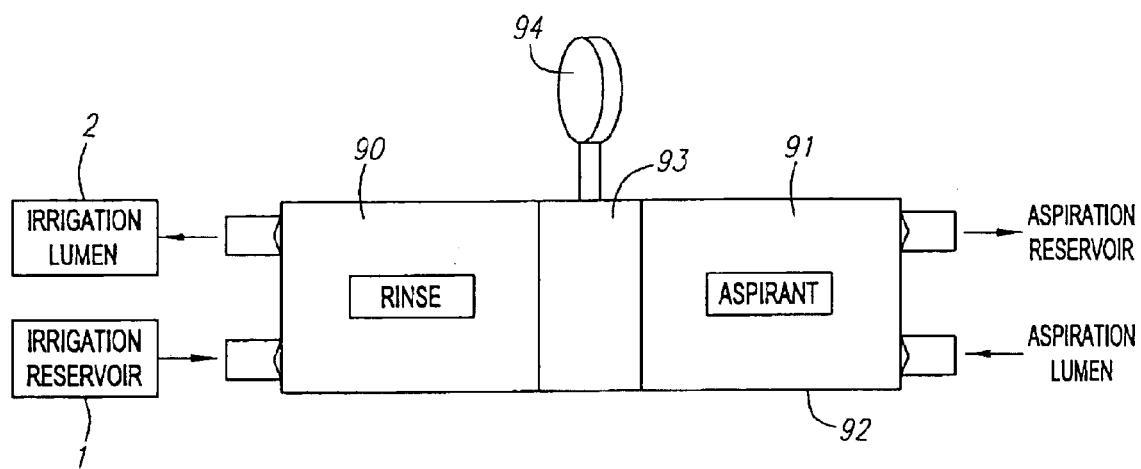
FIG. 14 is a device with both irrigant and aspirant chambers combined into one housing separated by a movable piston into two distinct chambers to allow for the simultaneous rinsing and aspirating.

FIG. 14 shows a side view of the device where the irrigation 90 and aspiration 91 fluid impermeable chambers are contained in the same, preferably rigid housing 92 and are separated by a centrally disposed piston 93 that engages the interior of the housing 92 about the entire periphery thereof to segregate the irrigant fluid from the aspirant fluid and allows the piston 93 to slide within the housing 92. By moving the piston 93 within the interior of the housing, typically from one extreme end to another, the irrigant is forced out of the irrigant chamber 90 and into the irrigation lumen 2. Fluid exchanged at the target site is collected through the aspiration lumens and into the aspirant chamber 91. Thus, in the example of FIG. 14, when the piston 93 slides from one end to the other, the irrigant chamber 90 expels irrigant, while the aspirant chamber 91 simultaneously draws in aspirant fluid. Then, as the piston 93 is moved back in the other direction, the irrigant chamber 91 refills itself with fluid from the irrigant reservoir 1 while the aspirant chamber 91 expels its contents into the aspiration reservoir 4. As in other embodiments described herein, this simple, compact arrangement allows for simultaneous irrigation and aspiration and yield a pulsatile flow. Although shown as a cylindrical housing 92, the construction and arrangement of the input, output, reservoir and piston elements could be altered without departing from the spirit of the invention. In the embodiment of FIG. 14, the piston is designed to move repeatedly and reproducibly within the housing to expel and collect a defined volume of fluid with each operation cycle.

The volume of fluid exchanged at the target site with each cycle of the piston 93 is substantially equivalent to the internal volume of the housing 92 assuming that the piston 93 is moved from one extreme to another extreme inside the housing 92 during each cycle of the operation of the device. This embodiment also demonstrates, as in the foregoing embodiments, that the fluid exchange device of the invention is readily adapted to be controlled either manually, in this case through the application of force to a handle 94 attached to the piston 93, or by electronic control, which in this embodiment would be provided by a simple pump or electrical or magnetic force to move the piston 91 within the housing 92. The separation of the irrigant and aspirant reservoirs 1, 4 from an irrigant and aspirant chamber 90, 91 permits the device to be repeatedly cycled to draw a defined volume into each chamber 90, 91 for propulsion through the irrigation lumen 2 and collection through the aspiration lumen 3. In an alternate embodiment, the entirety of the irrigant fluid to be exchanged at the target site would begin contained within an aspirant reservoir that is entirely located within the housing such that movement of the piston 91 from one extreme of the housing 92 to the other would communicate the entire volume of the irrigant reservoir 1 through the irrigation lumen 2, to the target exchange site, and back into the aspirant reservoir 4 via the aspiration lumen 3. A further example of this embodiment is shown in FIG. 15 below, having an alternate mechanical expedient for propelling fluid from the irrigant reservoir 1 into an aspirant reservoir 4.

Figure 15:
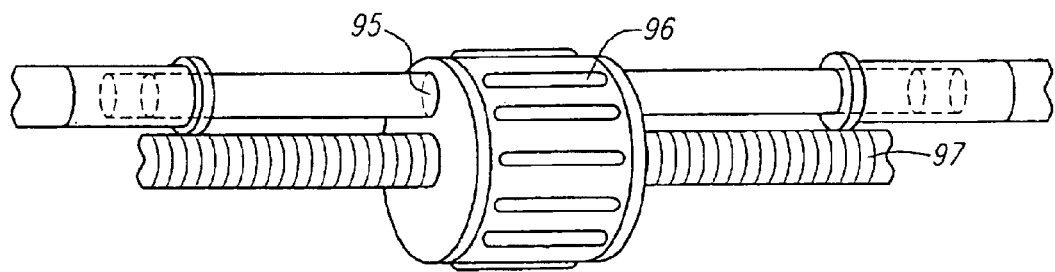
FIG. 15 shows a slidable and threaded combination configuration where an irrigant can be driven out and an aspirant simultaneously drawn in by both a sliding and a screw-type mechanism. The sliding provides gross travel and the rotation of the member about the axis produces a fine-tuning mechanism.

In the embodiment of FIG. 15, the irrigant and aspirant reservoirs 1,4 are separated by a fluid impermeable barrier 95 that is movable about a threaded axis 97 or other structure that passes within a slidable member 96 that rotates and slides about the threaded axis 97 to move the barrier 95 along the axis 97 to propel the irrigant fluid. Ideally, the slidable member 96 provide for a high rate of translation, while the member 97 provides for fine travel about the threaded axis 97. The sliding element can be selectively disengaged from the threads to allow it to slide rapidly along the threaded axis for gross adjustment. When engaged, the sliding element can be rotated for fine adjustment. Interior to the sliding element is a mechanism which permits this selective thread engagement by retracting the thread contact when activated.

Figure 16:
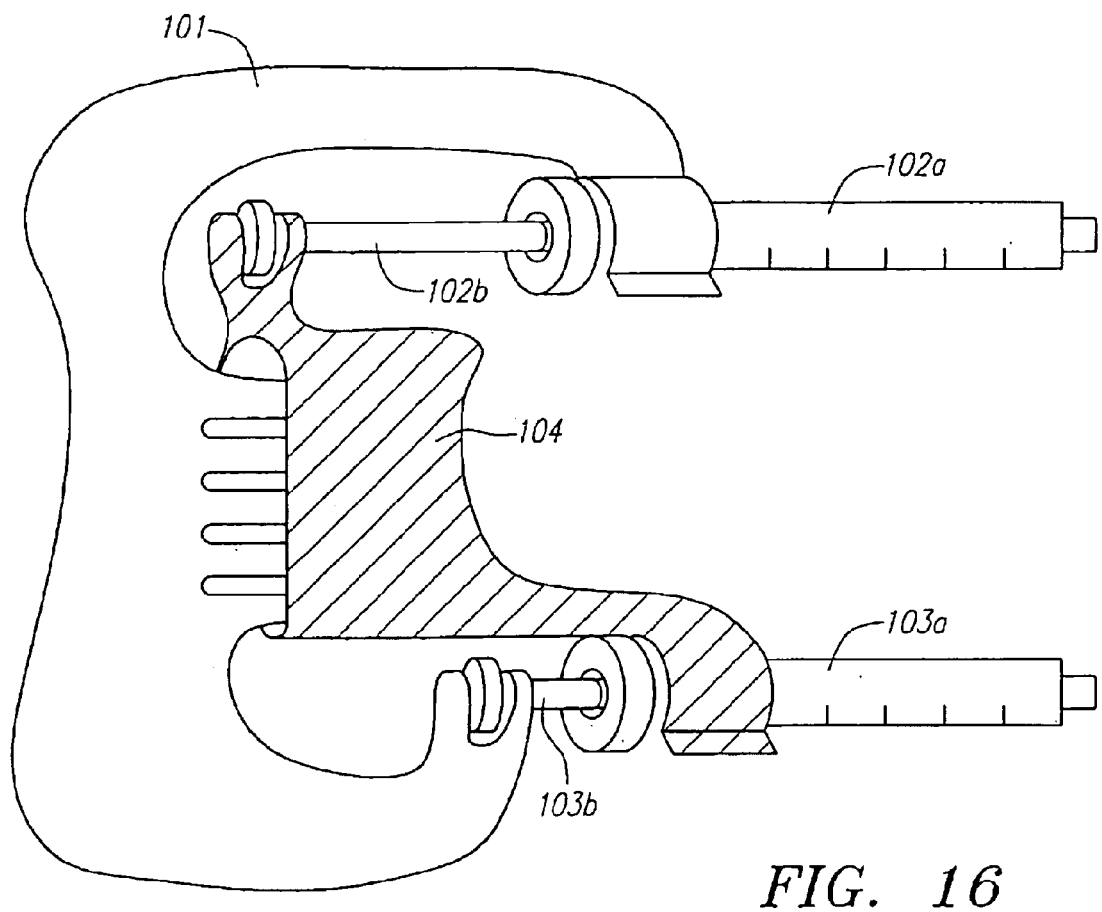
FIG. 16 is an embodiment of the fluid exchange device that can be comprised of as few as the structural elements that preferably attach to a cylinder body of one reservoir and piston of the other.

Referring to FIG. 15, this embodiment of the fluid exchange device is comprised of two main elements to achieve a configuration that allows for the body or cylinder actuation of both syringes in the desired and opposite manner. Essentially, a unitary body 101 connects of one syringe element 102*a* and is connected rigidly to the piston 103*b* of the other syringe element. A slidable element 104 engages the unitary body 101 and slides reproducibly in engagement therewith. As shown in FIG. 16, the slidable element 104 is also attached to the cylinder 103*a* of one syringe and the piston 102*b* of the other. Motion of the slidable element 104 exerts a force withdrawing one piston while advancing the other and braces the application of force by the attachment of the body 101 or element 104 to the cylinder or body of each syringe 102*a*, 103*a*. The design could incorporate existing syringes or have the syringe elements molded into the piece. There are several distinct advantages to this embodiment. One is that it ensures a 1:1 exchange ratio in terms of travel distance between the syringes. Another is that the geometric arrangement allows for a balancing of the forces involved in the device. Finally, the realization of the complex mechanics through just two moving parts is a significant advantage for the manufacturing and efficiency of the device.

Figure 17A:
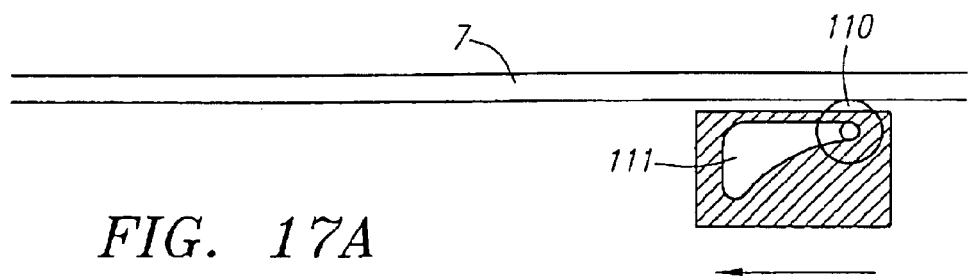
FIGS. 17A and 17B are a mechanical fixture for providing a self-advancing or retractors catheter element in combination with the fluid exchange device.

As described above, the element of turbulence is important to the efficacy of the device. Since fluids tend to assimilate to laminar flow, proximity of the irrigant ports or perforations that facilitates turbulence is important for optimal rinsing of the interior of a body structure. For this reason, translation of the catheter element may accompany the irrigation or aspiration or both. All embodiments described herein can be manually translated by means of the operator's hand. Additionally, the catheter can be translated using an automated translation system similar to those used in IVUS and similar applications. Alternatively, the catheter could be translated by an element incorporated into the fluid delivery device. Referring to FIG. 17A a simple mechanism that could be used to realize this self-advancing aspect. When the catheter 7 element is moved to the left in the direction of the arrows in FIG. 17A, the round engaging element 110 slides up in the slot 111 and engages the catheter 7 to move it to the left as well.

Figure 17B:
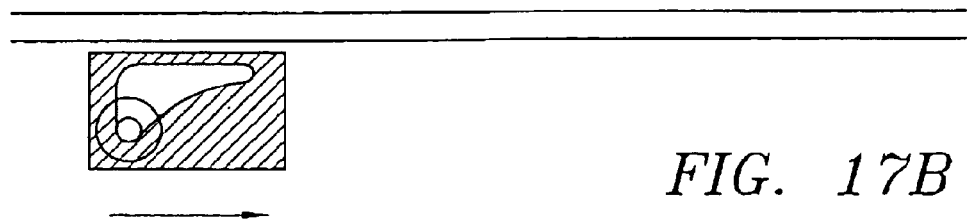

FIG. 17B shows the same mechanism. Once the catheter element 7 is slid to the right the round engaging element 110 slides down in the slot 11 and allows the catheter element 7 to slide freely to the right in the direction of the arrow without interacting or affecting the catheter's position. This allows for the selective retraction or advancement of the catheter 7 by a predetermined amount with each squeeze of the device. There are many ways in which this element could be realized. The simplest would be an apparatus that selectively grasps the catheter when moving one direction and idles or does not grasp when moving in the opposite direction. A guiding track that biases the element could be used to apply pressure and grasp the catheter moving in one direction and then release and allow idle sliding to the reset position in the other direction. This element could be selectively engaged by the operator when needed, and could be developed to allow for selection between advancement and retraction of the catheter.

Figure 18A:
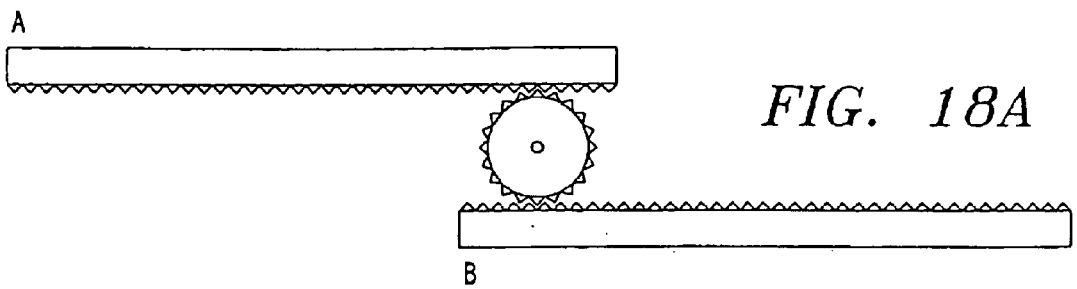
FIGS. 18A–18C are an embodiment of the invention with a staging capability such that the means for aspiration and irrigation are linked mechanically to travel in equivalent and opposite directions.
Figure 18B:
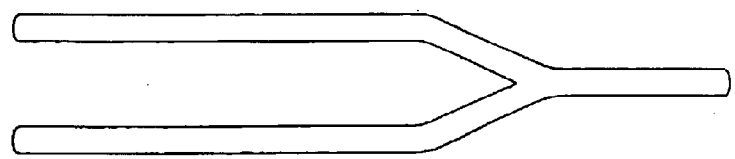
Figure 18C:
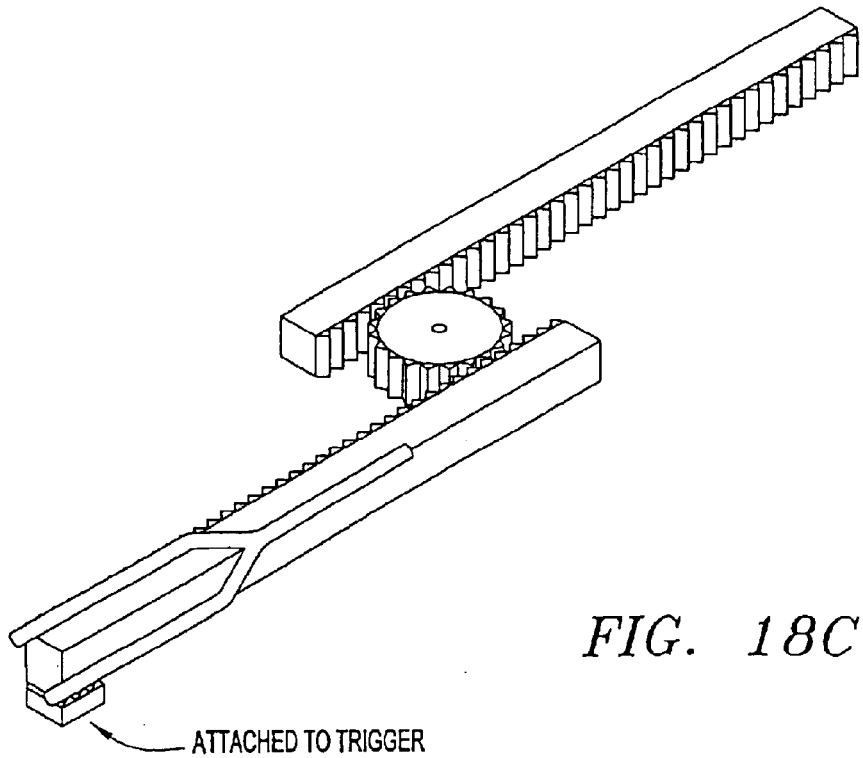

In the present preferred embodiment of the fluid exchange device, it is necessary to have a reset force supplied by an element such as a spring inherent in the device. This reset force is added to the resistance in the system that must be overcome by the operator to utilize the device. In some cases, an embodiment where this force was minimized or eliminated would allow more of the force generated by the operator to be directed to the work the device is performing and not to overcoming the reset force element. Referring to FIGS. 18A–18C, this function could be achieved through the use of a staged device. FIG. 18A shows a simple mechanical way in which the two sides of the device could be linked mechanically. It is important in this embodiment that the two sides be linked mechanically so that they behave in an equal and opposite manner. This is necessary so that the trigger can be actuated repeatedly in the same manner but engage just one of the sides while still driving the entire system. This allows the benefit of having the operator not realize the changes occurring internally in the device. The squeezes would not feel substantially different. In this embodiment, the first squeeze would activate the two chambers and the second squeeze would reset the two chambers. A simple mechanical setup could achieve this result. Similar mechanisms are commonly used in objects such as retractable ball point pens. Essentially, an element attached to the trigger element would be slightly biased to selectively engage one side or the other of the device. FIG. 18B shows a top view of the track layout that would guide the selectively engaging element of the trigger. With the two sides linked mechanically to travel in equivalent and opposite manners as described elsewhere, the force of the trigger element could always be applied in the same manner with varying effect. With the aid of the minimal return force element, the trigger is brought back to its full and extended position and biased to one side so that it will slip into the opposite track for the next actuation of the trigger. After that actuation, as the trigger is returning to its default position, it will be biased to one side of the device and slip easily into the track of the opposite side.

FIG. 18C is a diagram of how the system could be achieved such that each time the trigger is expanded, it engages the other side of the device and pulls it back when squeezed.

Many features have been listed with particular configurations, options, and embodiments. Any one or more of the features described may be added to or combined with any of the other embodiments or other standard devices to create alternate combinations and embodiments. Although the examples given include many specificities, they are intended as illustrative of only a few possible embodiments of the invention. Other embodiments and modifications will, no doubt, occur to those skilled in the art. Thus, the examples given should only be interpreted as illustrations of some of the preferred embodiments of the invention.

What is claimed is:

1. A fluid exchange device for fixed volume fluid exchange within a body lumen comprising:
   means for producing a pulsatile flow within the body lumen comprising:
   means for controlled delivery of a fixed volume of irrigant fluid from an irrigation reservoir through an irrigation lumen and an irrigation port located at the distal end of a catheter;
   means for controlled collection of a fixed volume of aspirant fluid from an aspiration port located in the distal end of the catheter through an aspiration lumen and into an aspiration reservoir, wherein the means for controlled delivery and means for controlled collection are linked and produce the fixed volume exchange of the irrigant fluid and the aspirant fluid by the pulsatile flow at a target fluid exchange site within the body lumen.

2. The device of claim 1 wherein the means for controlled delivery of a fixed volume of irrigant fluid is comprised of a member connected to a piston that propels irrigant fluid and that is linked to a piston that withdraws aspirant fluid.

3. The device of claim 2 wherein the means for controlled collection of a fixed volume aspirant fluid is comprised of a member connected to a piston that withdraws aspirant fluid and that is linked to the piston that propels irrigant fluid.

4. The device of claim 2 wherein the second member is connected to the body of a cylinder containing the piston that propels irrigant fluid.

5. The device of claim 1 wherein the means for controlled delivery of a fixed volume of irrigant fluid is a syringe in fluid communication with the irrigation lumen, and wherein the syringe is linked to the means for controlled collection of a fixed volume of aspirant fluid.

6. The device of claim 1 wherein the means for controlled collection of aspirant fluid is comprised of a syringe in fluid communication with the aspiration lumen, and wherein the syringe is linked to the means for controlled delivery of a fixed volume of irrigant fluid.

7. The device of claim 1 wherein the device comprises a trigger actuated to produce a predetermined volume of fluid exchange upon a single actuation of the trigger.

8. The device of claim 7 wherein the trigger is connected to a piston and actuation of the trigger applies force to the piston.

9. The device of claim 7 wherein the trigger is configured to be cyclically actuated to produce repeated and incremental fixed fluid exchanges through incremental movement of the piston.

* * * * *